US007297261B2

(12) United States Patent
Bomberger et al.

(10) Patent No.: US 7,297,261 B2
(45) Date of Patent: *Nov. 20, 2007

(54) SYSTEMS AND METHODS USING A SOLVENT FOR THE REMOVAL OF LIPIDS FROM FLUIDS

(75) Inventors: David C. Bomberger, Belmont, CA (US); Bryan Chavez, San Jose, CA (US); Pablo E. Garcia, Redwood City, CA (US); Eric Hegwer, Menlo Park, CA (US); Thomas P. Low, Belmont, CA (US); Ripudaman Malhotra, San Carlos, CA (US); Jeffrey J. Shimon, Mountain View, CA (US)

(73) Assignee: Lipid Sciences, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/700,626

(22) Filed: Jan. 31, 2007

(65) Prior Publication Data

US 2007/0138094 A1  Jun. 21, 2007

Related U.S. Application Data

(63) Continuation of application No. 11/263,819, filed on Nov. 1, 2005, now abandoned, which is a continuation of application No. 10/178,899, filed on Jun. 21, 2002, now abandoned.

(60) Provisional application No. 60/301,159, filed on Jun. 25, 2001.

(51) Int. Cl.
*B01D 63/02* (2006.01)
*B01D 36/00* (2006.01)
*B01D 11/04* (2006.01)
*B01D 11/00* (2006.01)

(52) U.S. Cl. ............... 210/252; 210/253; 210/255; 210/257; 210/263; 210/321.79; 210/321.8; 210/645; 210/649; 210/660; 210/805; 210/806; 604/5.03

(58) Field of Classification Search ............... None
See application file for complete search history.

(56) References Cited

U.S. PATENT DOCUMENTS 2,948,676 A * 8/1960 Hutson, Jr. ............... 208/322

(Continued)

FOREIGN PATENT DOCUMENTS

CA   1 271 708   7/1990

(Continued)

OTHER PUBLICATIONS

International Search Report for PCT/US02/19722, Oct. 1, 2002.

(Continued)

*Primary Examiner*—Krishnan S. Menon
(74) *Attorney, Agent, or Firm*—Kilpatrick Stockton LLP

(57) ABSTRACT

Systems and methods for removing lipids from a fluid, such as plasma, or from lipid-containing organisms. A fluid is combined with at least one extraction solvent, which causes the lipids to separate from the fluid or from lipid-containing organisms. The separated lipids are removed from the fluid. The extraction solvent is removed from the fluid or at least reduced to an acceptable concentration enabling the delipidated fluid to be administered to a patient without the patient experiencing undesirable consequences. Once the fluid has been processed, the fluid may be administered to a patient who donated the fluid, to a different patient, or stored for later use.

15 Claims, 15 Drawing Sheets

U.S. PATENT DOCUMENTS

| | | | |
|---|---|---|---|
| 3,647,624 | A | 3/1972 | Evenson |
| 3,958,939 | A | 5/1976 | Jones |
| 3,983,008 | A | 9/1976 | Shinozaki et al. |
| 3,989,466 | A | 11/1976 | Pan |
| 4,025,423 | A | 5/1977 | Stonner et al. |
| 4,103,685 | A | 8/1978 | Lupien et al. |
| 4,124,509 | A | 11/1978 | Iijima et al. |
| 4,234,317 | A | 11/1980 | Lucas et al. |
| 4,235,602 | A | 11/1980 | Meyer et al. |
| 4,258,010 | A | 3/1981 | Rozsa et al. |
| 4,350,156 | A | 9/1982 | Malchesky et al. |
| 4,391,711 | A | 7/1983 | Jackson et al. |
| 4,397,747 | A | 8/1983 | Ikeda |
| 4,399,217 | A | 8/1983 | Holmquist et al. |
| 4,402,940 | A | 9/1983 | Nose et al. |
| 4,435,289 | A | 3/1984 | Breslau |
| 4,463,988 | A | 8/1984 | Bouck et al. |
| 4,481,189 | A | 11/1984 | Prince |
| 4,522,809 | A | 6/1985 | Adamowicz et al. |
| 4,540,401 | A | 9/1985 | Marten |
| 4,540,573 | A | 9/1985 | Neurath et al. |
| 4,581,231 | A | 4/1986 | Purcell et al. |
| 4,591,505 | A | 5/1986 | Prince |
| 4,613,501 | A | 9/1986 | Horowitz |
| 4,615,886 | A | 10/1986 | Purcell et al. |
| 4,643,718 | A | 2/1987 | Marten |
| 4,645,512 | A | 2/1987 | Johns |
| 4,647,280 | A | 3/1987 | Maaskant et al. |
| 4,648,974 | A | 3/1987 | Rosskopf et al. |
| 4,658,012 | A | 4/1987 | Altorfer |
| 4,668,398 | A | 5/1987 | Silvis |
| 4,671,909 | A | 6/1987 | Torobin |
| 4,676,905 | A | 6/1987 | Nagao et al. |
| 4,677,057 | A | 6/1987 | Curtiss et al. |
| 4,680,320 | A | 7/1987 | Uku et al. |
| 4,696,670 | A | 9/1987 | Ohnishi et al. |
| 4,775,483 | A | 10/1988 | Mookerjea et al. |
| 4,832,034 | A | 5/1989 | Pizziconi et al. |
| 4,836,928 | A | 6/1989 | Aoyagi et al. |
| 4,879,037 | A | 11/1989 | Utzinger |
| 4,895,558 | A * | 1/1990 | Cham .................. 604/5.03 |
| 4,908,354 | A | 3/1990 | Seidel et al. |
| 4,909,940 | A | 3/1990 | Horowitz et al. |
| 4,909,942 | A | 3/1990 | Sato et al. |
| 4,923,439 | A * | 5/1990 | Seidel et al. ............ 604/5.03 |
| 4,935,204 | A | 6/1990 | Seidel et al. |
| 4,966,709 | A | 10/1990 | Nose et al. |
| 4,970,144 | A | 11/1990 | Fareed et al. |
| 5,026,479 | A | 6/1991 | Bikson et al. |
| 5,080,796 | A | 1/1992 | Nose et al. |
| 5,089,602 | A | 2/1992 | Isliker et al. |
| 5,112,956 | A | 5/1992 | Tang et al. |
| 5,116,307 | A | 5/1992 | Collins |
| 5,126,240 | A | 6/1992 | Curtiss |
| 5,128,318 | A | 7/1992 | Levine et al. |
| 5,151,023 | A | 9/1992 | Kuzuhara |
| 5,152,743 | A | 10/1992 | Gorsuch et al. |
| 5,187,010 | A | 2/1993 | Parham et al. |
| 5,203,778 | A | 4/1993 | Boehringer |
| 5,211,850 | A | 5/1993 | Shettigar et al. |
| 5,236,644 | A | 8/1993 | Parham et al. |
| 5,256,767 | A | 10/1993 | Salk et al. |
| 5,258,149 | A | 11/1993 | Parham et al. |
| 5,279,540 | A | 1/1994 | Davidson |
| 5,301,694 | A | 4/1994 | Raymond et al. |
| 5,354,262 | A | 10/1994 | Boehringer et al. |
| 5,391,143 | A | 2/1995 | Kensey |
| 5,393,429 | A | 2/1995 | Nakayama et al. |
| 5,401,415 | A | 3/1995 | Rauh et al. |
| 5,401,466 | A | 3/1995 | Foltz et al. |
| 5,418,061 | A | 5/1995 | Parham et al. |
| 5,419,759 | A | 5/1995 | Naficy |
| 5,424,068 | A | 6/1995 | Filip |
| 5,476,715 | A | 12/1995 | Otto |
| 5,484,396 | A | 1/1996 | Naficy |
| 5,496,637 | A | 3/1996 | Parham et al. |
| 5,523,096 | A | 6/1996 | Okarma et al. |
| 5,529,933 | A | 6/1996 | Young |
| 5,565,203 | A | 10/1996 | Gluck et al. |
| 5,634,893 | A | 6/1997 | Rishton |
| 5,637,224 | A | 6/1997 | Sirkar et al. |
| 5,652,339 | A | 7/1997 | Lerch et al. |
| 5,679,260 | A | 10/1997 | Boos et al. |
| 5,698,432 | A | 12/1997 | Oxford |
| 5,707,673 | A | 1/1998 | Prevost et al. |
| 5,719,194 | A | 2/1998 | Mann et al. |
| 5,744,038 | A * | 4/1998 | Cham .................. 210/634 |
| 5,753,227 | A | 5/1998 | Strahilevitz |
| 5,834,015 | A | 11/1998 | Oleske et al. |
| 5,853,725 | A | 12/1998 | Salk et al. |
| 5,855,782 | A | 1/1999 | Falkenhagen et al. |
| 5,858,238 | A | 1/1999 | McRea et al. |
| 5,877,005 | A | 3/1999 | Castor |
| 5,879,685 | A | 3/1999 | Gluck et al. |
| 5,885,578 | A | 3/1999 | Salk et al. |
| 5,891,432 | A | 4/1999 | Hoo |
| 5,895,650 | A | 4/1999 | Salk et al. |
| 5,911,698 | A | 6/1999 | Cham |
| 5,916,806 | A | 6/1999 | Salk et al. |
| 5,919,369 | A | 7/1999 | Ash |
| 5,928,930 | A | 7/1999 | Salk et al. |
| 5,948,441 | A | 9/1999 | Lenk et al. |
| 5,962,322 | A | 10/1999 | Kozarsky et al. |
| 5,980,478 | A | 11/1999 | Gorsuch et al. |
| 6,004,925 | A | 12/1999 | Dasseux et al. |
| 6,017,543 | A | 1/2000 | Salk et al. |
| 6,022,333 | A | 2/2000 | Kensey |
| 6,037,323 | A | 3/2000 | Dasseux et al. |
| 6,037,458 | A | 3/2000 | Hirai et al. |
| 6,039,946 | A | 3/2000 | Strahilevitz |
| 6,046,166 | A | 4/2000 | Dasseux et al. |
| 6,080,778 | A | 6/2000 | Yankner et al. |
| 6,127,370 | A | 10/2000 | Smith et al. |
| 6,136,321 | A | 10/2000 | Barrett et al. |
| 6,139,746 | A | 10/2000 | Kopf |
| 6,156,727 | A | 12/2000 | Garber et al. |
| 6,165,502 | A | 12/2000 | Oleske et al. |
| 6,171,373 | B1 | 1/2001 | Park et al. |
| 6,193,891 | B1 | 2/2001 | Kent et al. |
| 6,264,623 | B1 | 7/2001 | Strahilevitz |
| 6,309,550 | B1 | 10/2001 | Ivensen et al. |
| 6,337,368 | B1 | 1/2002 | Kobayashi et al. |
| 6,440,387 | B1 | 8/2002 | Yankner et al. |
| 6,472,421 | B1 | 10/2002 | Wolozin |
| 6,605,588 | B1 | 8/2003 | Lees et al. |
| 6,706,008 | B2 | 3/2004 | Vishnoi et al. |
| 6,737,066 | B1 | 5/2004 | Moss |
| 6,913,696 | B1 * | 7/2005 | Korngold et al. .......... 210/640 |
| 6,991,727 | B2 * | 1/2006 | Bomberger et al. .... 210/321.78 |
| 7,033,500 | B2 * | 4/2006 | Bomberger et al. .... 210/321.79 |
| 7,166,223 | B2 * | 1/2007 | Bomberger et al. ......... 210/634 |
| 7,195,710 | B2 * | 3/2007 | Bomberger et al. ...... 210/257.2 |
| 2001/0028895 | A1 | 10/2001 | Bisgaier et al. |
| 2002/0055529 | A1 | 5/2002 | Bisgaier et al. |
| 2002/0081263 | A1 | 6/2002 | Yankner et al. |
| 2002/0107173 | A1 | 8/2002 | Friedhoff et al. |
| 2002/0183379 | A1 | 12/2002 | Yankner et al. |
| 2002/0188012 | A1 | 12/2002 | Bisgaier et al. |
| 2003/0018013 | A1 | 1/2003 | Dasseux et al. |

FOREIGN PATENT DOCUMENTS

| | | |
|---|---|---|
| CN | 1189378 | 8/1998 |
| DE | 29 44 138 A1 | 6/1981 |

| | | | |
|---|---|---|---|
| DE | 31 18 072 A1 | 11/1982 |
| DE | 32 13 390 A1 | 10/1983 |
| DE | 33 10 263 A1 | 9/1984 |
| EP | 0 036 283 A2 | 9/1981 |
| EP | 0 267 471 A1 | 5/1988 |
| FR | 2 571 971 A1 | 4/1986 |
| GB | 1183506 | 3/1970 |
| JP | 127104 | 1/1980 |
| JP | 277303 | 10/1993 |
| SU | 1116396 A | 9/1984 |
| SU | 1204224 A | 1/1986 |
| SU | 1752187 A3 | 7/1992 |
| WO | WO 88/09345 A1 | 12/1988 |
| WO | WO 95/03840 A1 | 2/1995 |
| WO | WO 99/38498 A1 | 8/1999 |
| WO | 00/57995 | 10/2000 |
| WO | WO 01/45718 A1 | 6/2001 |
| WO | WO 01/56579 A1 | 8/2001 |
| WO | WO 02/10768 A3 | 2/2002 |
| WO | WO 02/30863 A2 | 4/2002 |
| WO | WO 02/062824 A2 | 8/2002 |

OTHER PUBLICATIONS

Agnese, et al., Clinical Biochemistry, Evaluation of Four Reagents for Delipidation of Serum, 16, 98-100, (1983).
Albouz, et al., Ann. Biol. Clin., Extraction of Plasma Lipids Preserving Antigenic Properties of Proteins and Allowing Quantitation of Gangliosides by Neuraminic Acid Determination, 37, 287-290. (abstract only) (1979).
Aloia, et al., Lipid Composition and Fluidity of the Human Immunodeficiency Virus Envelope and Host Cell Plasma Membranes, Proc. Natl. Acad. Sci. U.S.A., Jun. 1993, pp. 5181-5185, vol. 90. Blanche et al., "Characterization of Complexes of Egg Yolk Phosphatidylcholine and Apolipoprotein A-II Prepared in the Absence and Presence of Sodium Cholate", Biochimica et Biophysica Acta, 1988, pp. 143-152, vol. 958.
Andre et al., Journal of Virology, Characterization of Low- and Very-Low-Density Hepatitis C Virus RNA-Containing Particles, 76 (14), 6919-6928. (Jul. 2002).
Asztalos et al., Arterioscler. Thromb. Vasc. Biol., Distribution of Apo A-I-Containing HDL Subpopulations in Patients with Coronary Heart Disease, 2670-2676. (Dec. 1, 2000).
Asztalos et al., Arterioscler. Thromb. Vasc. Biol., Presence and Formation of 'Free Apolipoprotein A-I-Like' Particles in Human Plasma, 15, 1419-1423. (1995).
Asztalos et al., Arterioscler. Thromb. Vasc. Biol., Role of Free Apolipoprotein A-I in Cholesterol Efflux, 17, 1630-1636. (1997).
Badimon, et al., Laboratory Investigation, High Density Lipoprotein Plasma Fractions Inhibit Aortic Fatty Streaks in Cholesterol-Fed Rabbits, 60, 455-461. (1989).
Badimon, et al., J. Clinical Investigation, Regression of Atherosclerotic Lesions by High Density Lipoprotein Plasma Fraction in the Cholesterol-Fed Rabbit, 85, 1234-1241. (1990).
Barrans et al., Biochimica et Biophysica Acta, Pre-β HDL: Structure and Metabolism, 1300, 73-85. (1996).
Barres et al., Science, Cholesterol—Making or Breaking the Synapse, 294, 1296/1297. (Nov. 9, 2001).
Blanche et al., "Characterization of Complexes of Egg Yolk Phosphatidylcholine and Apolipoprotein A-II Prepared in the Absence and Presence of Sodium Cholate", Biochimica et Biophysica Acta, 1988, pp. 143-152, vol. 958. Rye, et al. "Changes in the Size of Reconstituted High Density Lipoproteins During Incubation with Cholesteryl Ester Transfer Protein: the Role of Apolipoproteins", 1992, pp. 215-224, vol. 33.
Bloom, et al., Clin. Biochem., Quantitation of lipid profiles from isolated serum lipoproteins using small volumes of human serum, 14, 119-125. (abstract only) (Jun. 1981).
Burns et al., Neurochem Res, Use of in Vivo Models to Study the Role of Cholesterol in the Etiology of Alzheimer's Disease 28, 979-86. (abstract only) (Jul. 2003).

Cham, Clinical Chemistry, Nature of the Interaction Between Low-Density Lipoproteins and Polyanions and Metal Ions, as Exemplified by Heparin and $Ca^{2+}$, 22, 1812-1816. (1976).
Cham, et al., J. of Lipid Research, A Solvent System for Delipidation of Plasma or Serum Without Protein Precipitation, 17, 176-181. (1976).
Cham, et al., Clinical Chemistry, Changes in Electrophoretic Mobilities of α- and β-Lipoproteins as a Result of Plasma Delipidation, 22, 305-309. (1976).
Cham, et al., Biochemical and Biophysical Research Communications, Heterogeneity of Lipoprotein B, 103, 196-206. (1981).
Cham, et al., Chem. Biol. Interactions, Importance of Apolipoproteins in Lipid Metabolism, 20, 263-277. (1978).
Cham, et al., J. Biol. Chem., In Vitro Partial Relipidation of Apolipoproteins in Plasma, 251, 6367-6371. (abstract only) (1976).
Cham, et al., Pharmacol. (Life Sci. Adv.), Lipid Apheresis in an Animal Model Causes Acute Reduction in plasma Lipid Concentrations and Mobilisation of Lipid from Liver and Aorta, 13, 25-32. (1994).
Cham, et al., J. Clin. Apheresis, Lipid Apheresis in an Animal Model Causes In Vivo Changes in Lipoprotein Electrophoretic Patterns, 11, 61-70. (1996).
Cham, et al., J. Clin. Apheresis, Lipid Apheresis: An In Vivo Application of Plasma Delipidation with Organic Solvents Resulting in Acute Transient Reduction of Circulating Plasma Lipids in Animals, 10, 61-69. (1995).
Cham, et al., Clinical Chemistry, Phospholipids in EDTA—Treated Plasma and Serum, 39, 2347-2348. (1993).
Cham, et al., 59th Congress European Atherosclerosis Society, Nice, France, Rapid Regression of Atherosclerosis by Cholesterol Apheresis—A Newly Developed Technique, 17-21. (abstract only) (May 1992).
Cham, et al., Clinica Chimica Acta, Rapid, Sensitive Method for the Separation of Free Cholesterol from Ester Cholesterol, 49, 109-113. (1973).
Clay et al., "Formation of Apolipoprotein-Specific High-Density Lipoprotein Particles from Lipid-Free Apolipoproteins A-I and AII", Biochem Journal, 1999, pp. 445-451, vol. 337.
Collet et al., Journal of Biological Chemistry, Differential Effects of Lecithin and Cholesterol on the Immunoreactivity and Confirmation of Apolipoprotein A-I in High Density Lipoproteins, 266 (14), 9145-9152. (May 15, 1991).
Cooper, Drugs Aging, Dietary Lipids in the Aetiology of Alzheimer's Disease: Implications for Therapy, 20 (6), 399-418. (abstract only) (2003).
Cruzado et al., Analytical Biochemistry, Characterization and Quantitation of the Apoproteins of High-Density Lipoprotein by Capillary Electrophoresis, 14 (7), 100-109. (1996).
Dass, C.R., Apolipoprotein A-1, Phospholipid Vesicles, and Cyclodextrins as Potential Anti-Atherosclerotic Drugs: Delivery, Pharmacokinetics, and Efficacy, Drug Deliv. Jul.-Sep. 2000; 7(3): 161-82.
Deva, et al., J. Hosp. Infect., Establishment of an in-use testing method for evaluating disinfection of surgical instruments using the duck hepatitis B model, 22, 119-130. (abstract only) (Jun. 1996).
Durbin, et al., "Lipid-Free Apolipoproteins A-I and A-II Promote Remodeling of Reconstituted High Density Lipoproteins and Alter Their Reactivity with Lecithin: Cholestoral Acyltransferase", 1999, pp. 2293-2302, vol. 40.
Durbin, et al., "The Effect of Apolipoprotein A-II on the Structure and Function of Apolipoprotein A-I in a Homogeneous Reconstituted High Density Lipoprotein Particle", The Journal of Biological Chemistry, 1997, pp. 31333-31339, vol. 272, No. 50.
Dwivedy, 18th Australian Atherosclerosis Society Conference, Surfers Paradise, Increase of Reverse Cholesterol Transport by Cholesterol Apheresis Regression of Atherosclerosis, 21. (1992).
Eisenhauer, et al, Klin Wochenschr (KWH), Selective Removal of Low Density Lipoproteins (LDL) by Precipitation at Low pH: First Clinical Application of the HELP System, 65, 161-168. (1987).
Fang, et al., 18th Australian Atherosclerosis Society Conference, Gold Coast, Australia, In Vivo Rapid Mobilization of Adipose Tissue by Lipid Apheresis—A Newly Developed Technique. (1992).

Feinberg, et al. AIDS Vaccine Models: Challenging Challenge Viruses, nature Medicine, Mar. 2002, 8(3): 207-210.

Feinstone, et al., Infection and Immunity, Inactivation of Hepatits B Virus and Non-A, Non-B Hepatitis by Chloroform, 41, 816-821. (Aug. 1983).

Golde et al., Drug Discovery Today, Cholesterol Modulation as an Emerging Strategy for the Treatment of Alzheimer's Disease, 6 (20), 1049-1055. (abstract only) (Oct. 15, 2001).

Hatch et al., Lipoprotein Analysis, Advances in Lipid Research, Practical Methods for Plasma Lipoprotein Analysis, 6, 1-68. (1968).

Horowitz, et al., Blood Coagulation and Fibrinolysis, Viral safety of solvent/detergent-treated blood products, 5, S21-S28. (1994).

Innerarity, et al., Biochemistry, Enhanced Binding by Cultured Human Fibroblasts of Apo-E-Containing Lipoproteins as Compared with Low Density Lipoproteins, 17, 1440-1447. (1978).

Ito J., Nagayasu Y. et al. Cholesterol-Sphingomyelin Interaction in Membrane and Apolipoprotein-Mediated Cellular Cholesterol Efflux, J Lipid Res., Jun. 2000; 41(6): 894-904.

Jackson et al., Biochimica et Biophysica Acta, Isolation and Characterization of the Major Apolipoprotein from Chicken High Density Lipoproteins, 420, 342-349. (1976).

Klimov, et al., Kardologila, Extraction of Lipids from Blood Plasma and Subsequent Introduction of Autologous Delipidized Plasma into the Body as a Possible Means to Treat Atherosclerosis [translation], 18, 23-29. (1978).

Koizumi, et al., J. Lipid Research, Behavior of Human Apolipoprotein A-1: Phospho-Lipid and apoHDL: Phospholipid Complexes In Vitro and After Injection into Rabbits, 29, 1405-1415. (1988).

Kostner, et al., XI Internet Symp. on Drugs Affecting Lipid Metabolism, Italy, Increases of APO A1 Concentration in Hypercholesteraemic Chickens after Treatment with a Newly Developed Extracorpreal Lipid Elimination. (May 13, 1992).

Kostner, et al., European Journal of Clinical Investigation, Lecithin-cholesterol acyltransferase activity in Normocholesterolaemic and Hypercholesterolaemic Roosters: Modulation by Lipid Apheresis, 27, 212-218. (May 7, 1997).

Koudinov et al., Clin Chim Acta, Alzheimer's Amyloid Beta Interaction with Normal Human Plasma High Density Lipoprotein: Association with Apolipoprotein and Lipids, 270 (2), 75-84. (abstract only) (Feb. 23, 1999).

Koudinov et al., Cell Biol Int., Alzheimer's Soluble Amyloid Beta Protein is Secreted by HepG2 Cells as an Apolipoprotein, 21 (5), 265-71. (abstract only) (May 1997).

Koudinov et al., Biochem Biophys Res Commun, Biochemical Characterization of Alzheimer's Soluble Amyloid Beta Protein in Human Cerebrospinal Fluid: Association with High Density Lipoproteins, 223 (3), 592-7. (abstract only) (Jun. 25, 1999).

Koudinov et al., Science, Cholesterol's Role in Synapse Formation, 294, 2213. (Nov. 9, 2001).

Koudinova et al., Soc. Neuroscience Abstract Viewer and Itinerary Planner, Amyloid Beta, Neural Lipids, Cholesterol and Alzheimer's Disease—Abstract No. 21.10. (2002).

Lipid Sciences, http://www.lipidsciences.com/technology.html, Lipid Technology, 1-4. (Aug. 25, 2001).

Lupien, et al., Lancet (LOS), A New Approach to the Management of Familial Hypercholesterolaemia: Removal of Plasma-Cholesterol Based on the Principle of Affinity Chromatography, 1, 1261-1265. (1976).

Matz et al., "Reaction of Human Lecithin Cholesterol Acyltransferase with Synthetic Micellar Complexes of Apolipoprotein A-I, Phosphatidylcholine, and Cholesterol", The Journal of Biological Chemistry, 1982, pp. 4541-4546, vol. 257, No. 8.

Mauch et al., Science, CNS Synaptogenesis Promoted by Glia-Derived Cholesterol, 294, 1354-1357. (Nov. 9, 2001).

Moya et al., Arteriosclerosis and Thrombosis, A Cell Culture System for Screening Human Serum for Ability to Promote Cellular Cholesterol Efflux, 14 (7), 1056-1065. (Jul. 1994).

Nester, et al. Microbiology, 1983, pp. 585.

Neurath et al, Properties of Delipidated Hepatitis B Surface Antigen (HBsAg) and Preparation of Its Proteolytic Cleavage Fragments Carrying HbsAg-Specific Antigenic Determinants, Intervirology, 1978, pp. 265-275, vol. 10.

Ngu, Medical Hypotheses, Chronic Infections from the Perspective of Evolution: a Hypothesis, 42, 81-88. (1994).

Ngu, Medical Hypotheses, Human Cancers and Viruses: A Hypothesis for Immune Destruction of Tumours Caused by Certain Enveloped Viruses Using Modified Viral Antigens, 39, 17-21. (1992).

Ngu, Medical Hypotheses, The viral envelope in the evolution of HIV: a hypothetical approach to inducing an effective immune response to the virus, 48, 517-521. (1997).

Okazaki et al., Journal of Chromatography, Biomedical Applications, Improved High-Performance Liquid Chromatographic Method for the Determination of Apolopoproteins in Serum High-Density Lipoproteins, 430, 135-142. (1988).

Osborne, et al., "Delipidation of Plasma Lipoproteins", Methods in Enzymology, 1986, pp. 213-222, vol. 128.

Parker, et al., Proceedings of the National Academy of Sciences, Plasma High Density Lipoprotein is Increased in Man When Low Density Lipoprotein (LDL) is Lowered by LDL-Pheresis, 83, 777-781. (1986).

Paterno et al., Department of Clinical and Experimental Medicine, Reconstituted High-Density Lipoprotein Exhibits Neuroprotection in Two Rat Models of Stroke. (Abstract only) (Dec. 29, 2003).

Refolo et al., Soc. Neuroscience Abstracts, Cholesterol Metabolism: A Potential Target for Alzheimer's Disease Therapy, 27 (2), 1518. (abstract only) (2001).

Robern et al., Experientia, The Application of Sodium Deoxycholate and Sephacryl-200 for the Delipidation and Separation of High Density Lipoproteins, 38, 437-439. (1982).

Ryan, et al., Clinical Chemistry, An Improved Extraction Procedure for the Determination of Triglycerides and Cholesterol in Plasma or Serum, 13, 769-772. (1967).

Scanu et al., Analytical Biochemistry, Solubility in Aqueous Solutions of Ethanol of the Small Molecular Weight Peptides of the Serum Very Low Density and High Density Lipoproteins: Relevance to the Recovery Problem During Delipidation of Serum Lipoproteins, 44, 576-588. (1971).

Segrest et al., Journal of Biological Chemistry, A Detailed Molecular Belt Model for Apolipoprotein A-I in Discoidal High Density Lipoprotein, 274 (45), 31755-31758. (Nov. 5, 1999).

Slater, et al., J. of Lipid Research, A Comparison of Delipidated Sera Used in Studies of Sterol Synthesis by Human Mononuclear Leukocytes, 20, 413-416. (1979).

Slater, et al., Atherosclerosis, The Effect of Delipidated High Density Lipoprotein on Human Leukocyte Sterol Synthesis, 35, 41-49. (1980).

Thompson, et al., Lancet (LOS), Plasma Exchange in the Management of Homozygous Familial Hypercholesterolaemia, 1, 1208-1211. (1975).

Tricerri, M.A. et al., Interaction of Apolipoprotein A-1 in Three Different Conformations with Palmitoly Oleoyl Phosphatidylcholine Vesicles, J Lipid Res. 2002; 43(2): 187-97.

Walker, et al., "Escape from the Immune System", Nature, Sep. 21, 2000, pp. 313-314, vol. 407.

Williams, et al., Proc. Natl. Acad. Sci. USA, Low Density Lipoprotein Receptor-Independent Hepatic Uptake of a Synthetic, Cholesterol-Scavenging Lipoprotein: Implications for the Treatment of Receptor-Deficient Atherosclerosis, 85, 242-246. (1988).

Williams et al., Biochim. Biophys. Act., Uptake of Endogenous Cholesterol by a Synthetic Lipoprotein, 875 (2), 183-194. (Feb. 23, 1986).

Wong, et al, Journal of Lipid Research, Retention of gangliosides in serum delipidated by diisopropyl ether-1-butanol extraction, 24, 666-669. (1983).

Yokoyama, et al., Arterioclerosis, Selective Removal of Low Density Lipoprotein by Plasmapheresis in Familial Hypercholesterolemia, 5, 613-622. (1985).

Yoshidome et al., Artif Organs, Serum Amyloid A and P Protein Levels are Lowered by Dextran Sulfate Cellulose Low-Density Lipoprotein Apheresis, 22 (2), 144-148. (1998).

Zetia, http://www.zetia.com/ezetimbe/zetia/hcp/product_highlights/index.jsp, Zetia (ezetimibe), 1-2. (Jul. 18, 2003).

Zetia, http://www.zetia.com/ezetimibe/zetia.hcp/mechanism_of_action/index.jsp, Zetia: Compliments Statin with a Unique Mechanism, 1-2. (Jul. 18, 2003).

Zhang et al., Journal of Lipid Research, Characterization of phospholipids in a pre-alpha HDL: Selective Phospholipid Efflux with Apolipoprotein A-I, 39, 1601-1607. (1998).

* cited by examiner

SYSTEMS AND METHODS USING A SOLVENT FOR THE REMOVAL OF LIPIDS FROM FLUIDS

This application is a continuation application of U.S. application Ser. No. 11/263,819, filed Nov. 1, 2005, now abandoned which is a continuation application of U.S. application Ser. No. 10/178,899, filed Jun. 21, 2002, now abandoned, which claims priority to U.S. Provisional Patent Application No. 60/301,159, filed Jun. 25, 2001, the entire contents of each of which are incorporated by reference herein.

FIELD OF THE INVENTION

This invention relates to systems, apparatuses and methods for the removal of lipids from fluids, especially plasma, or from lipid-containing organisms, or both, using a single extraction solvent. After being processed, the fluid may be administered to an animal or human for therapeutic use such as treatment of arteriosclerosis and atherosclerotic vascular diseases, removal of fat within an animal or human, and reduction of infectivity of lipid-containing organisms.

BACKGROUND OF THE INVENTION

Hyperlipidemia and Arteriosclerosis

Cardiovascular, cerebrovascular, and peripheral vascular diseases are responsible for a significant number of deaths annually in many industrialized countries. One of the most common pathological processes underlying these diseases is arteriosclerosis. Arteriosclerosis is characterized by lesions, which begin as localized fatty thickenings in the inner aspects of blood vessels supplying blood to the heart, brain, and other organs and tissues throughout the body. Over time, these atherosclerotic lesions may ulcerate, exposing fatty plaque deposits that may break away and embolize within the circulation. Atherosclerotic lesions obstruct the lumens of the affected blood vessels and often reduce the blood flow within the blood vessels, which may result in ischemia of the tissue supplied by the blood vessel. Embolization of atherosclerotic plaques may produce acute obstruction and ischemia in distal blood vessels. Such ischemia, whether prolonged or acute, may result in a heart attack or stroke from which the patient may or may not recover. Similar ischemia in an artery supplying an extremity may result in gangrene requiring amputation of the extremity.

For some time, the medical community has recognized the relationship between arteriosclerosis and levels of dietary lipid, serum cholesterol, and serum triglycerides within a patient's blood stream. Many epidemiological studies have been conducted revealing that the amount of serum cholesterol within a patient's blood stream is a significant predictor of coronary disease. Similarly, the medical community has recognized the relationship between hyperlipidemia and insulin resistance, which can lead to diabetes mellitus. Further, hyperlipidemia and arteriosclerosis have been identified as being related to other major health problems, such as obesity and hypertension.

Hyperlipidemia may be treated by changing a patient's diet. However, use of a patient's diet as a primary mode of therapy requires a major effort on the part of patients, physicians, nutritionists, dietitians, and other health care professionals and thus undesirably taxes the resources of health professionals. Another negative aspect of this therapy is that its success does not rest exclusively on diet. Rather, success of dietary therapy depends upon a combination of social, psychological, economic, and behavioral factors. Thus, therapy based only on correcting flaws within a patient's diet is not always successful.

In instances when dietary modification has been unsuccessful, drug therapy has been used as an alternative. Such therapy has included use of commercially available hypolipidemic drugs administered alone or in combination with other therapies as a supplement to dietary control. Hypolipidemic drugs have had varying degrees of success in reducing blood lipid; however, none of the hypolipidemic drugs successfully treats all types of hyperlipidemia. While some hypolipidemic drugs have been fairly successful, the medical community has not found any conclusive evidence that hypolipidemic drugs cause regression of atherosclerosis. In addition, all hypolipidemic drugs have undesirable side effects. As a result of the lack of success of dietary control, drug therapy and other therapies, atherosclerosis remains a major cause of death in many parts of the world.

To combat this disturbing fact, a relatively new therapy has been used to reduce the amount of lipid in patients for whom drug and diet therapies were not sufficiently effective. This therapy, referred to as plasmapheresis therapy or plasma exchange therapy, involves replacing a patient's plasma with donor plasma or more usually a plasma protein fraction. While having been fairly successful, this treatment has resulted in complications due to introduction of foreign proteins and transmission of infectious diseases. Further, plasma exchange undesirably removes many plasma proteins, such as very low-density lipoprotein (VLDL), low-density lipoprotein (LDL), and high-density lipoprotein (HDL).

HDL is secreted from both the liver and the intestine as nascent, disk-shaped particles that contain cholesterol and phospholipids. HDL is believed to play a role in reverse cholesterol transport, which is the process by which excess cholesterol is removed from tissues and transported to the liver for reuse or disposal in the bile. Therefore, removal of HDL from plasma is not desirable.

Other apheresis techniques exist that can remove LDL from plasma. These techniques include absorption of LDL in heparin-agarose beads (affinity chromatography), the use of immobilized LDL-antibodies, cascade filtration absorption to immobilize dextran sulphate, and LDL precipitation at low pH in the presence of heparin. Each method removes LDL but not HDL.

LDL apheresis, however, has disadvantages. For instance, significant amounts of plasma proteins in addition to LDL are removed during apheresis. In addition, LDL apheresis must be performed frequently, such as weekly, to obtain a sustained reduction in LDL-cholesterol. Furthermore, LDL removal may be counterproductive because low LDL levels in a patient's blood may result in increased cellular cholesterol synthesis. Thus, removal of LDL from a patient's blood may have negative side effects.

Yet another method of achieving a reduction in plasma cholesterol in homozygous familial hypercholesterolemia, heterozygous familial hypercholesterolemia and patients with acquired hyperlipidemia is an extracorporeal lipid elimination process, referred to as cholesterol apheresis. In cholesterol apheresis, blood is withdrawn from a patient, the plasma is separated from the blood, and the plasma is mixed with a solvent mixture. The solvent mixture extracts lipids from the plasma. Thereafter, the delipidated plasma is recombined with the patient's blood cells and returned to the patient.

More specifically, lipid apheresis results in the removal of fats from plasma or serum. However, unlike LDL apheresis, the proteins (apolipoproteins) that transport lipids remain soluble in the treated plasma or serum. Thus, the apolipoproteins of VLDL, LDL and HDL are present in the treated plasma or serum. These apolipoproteins, in particular apolipoproteins A1 from the delipidated HDL in the plasma or serum, are responsible for the mobilization of unwanted lipids or toxins, such as excessive amounts of deposited lipids including cholesterol in arteries, plaques, and excessive amounts of triglycerides, adipose tissue, and fat soluble toxins present in adipose tissue. These excessive amounts of lipids or toxins are transferred to the plasma or serum, and then bound to the newly assembled apolipoproteins. Application of another lipid apheresis procedure successively removes these unwanted lipids or toxins from the plasma and thus the body. The main advantage of this procedure is that LDL and HDL are not removed from the plasma. Instead, only cholesterol, some phospholipid and a considerable amount of triglycerides are removed.

While lipid apheresis has the potential to overcome the shortcomings of dietary control, drug therapy and other apheresis techniques, existing apparatuses and methods for lipid apheresis do not provide a sufficiently rapid and safe process. Thus, a need exists for systems, apparatuses and methods capable of conducting lipid apheresis more quickly than accomplished with conventional equipment and methods.

Unfortunately, existing lipid apheresis systems suffer from a number of disadvantages that limit their ability to be used in clinical applications, such as in doctors' offices and other medical facilities. One disadvantage is the explosive nature of the solvents used to delipidate this plasma. If used in a continuous system, these solvents are in close proximity to patients and medical staff. Thus, it would be advantageous to limit this exposure; however, this hazard is clearly present for the duration of the delipidation process, which usually runs for several hours.

Another disadvantage is the difficulty in removing a sufficient amount of solvents from the delipidated plasma in order for the delipidated plasma to be safely returned to a patient. In addition, patients are subjected to an increased chance of prolonged exposure to solvents in a continuous system. Furthermore, current techniques do not provide for sequential multi-washes because the volume of blood necessary for continuous processing using conventional equipment requires removal of an amount of blood that would harm the patient. In other words, conventional equipment does not allow for automated continuous removal, processing and return of plasma to a patient in a manner that does not negatively impact total blood volume of the patient. While the long-term toxicity of various extraction solvents is not known, especially when present in the bloodstream, clinicians know that some solvents may cross the blood-brain barrier. Furthermore, external contact with solvents is known to cause clinical symptoms, such as irritation of mucous membranes, contact dermatitis, headaches, dizziness and drowsiness. Therefore, conventional equipment for lipid apheresis is not adequate to conduct continuous processing of a patient's blood.

Infectious Disease

While the medical community has struggled to develop cures for hyperlipidemia and arteriosclerosis, it has likewise struggled in its battle against infectious diseases. Infectious diseases are a major cause of suffering and death throughout the world. Infectious disease of varied etiology affects billions of animals and humans each year and inflicts an enormous economic burden on society. Many infectious organisms contain lipid as a major component of the membrane that surrounds them. Three major classes of organisms that produce infectious disease and contain lipid in their cell wall or envelope include bacteria, viruses, and protozoa. Numerous bacteria and viruses that affect animals and humans cause extreme suffering, morbidity and mortality. Many bacteria and viruses travel throughout the body in fluids, such as blood, and some reside in plasma. These and other infectious agents may be found in other fluids, such as peritoneal fluid, lymphatic fluid, pleural fluid, pericardial fluid, cerebrospinal fluid, and in various fluids of the reproductive system. Disease can be caused at any site bathed by these fluids. Other bacteria and viruses reside primarily in different organ systems or in specific tissues, where they proliferate and enter the circulatory system to gain access to other tissues and organs.

Infectious agents, such as viruses, affect billions of people annually. Recent epidemics include the disease commonly known as acquired immune deficiency syndrome (AIDS), which is believed to be caused by the human immunodeficiency virus (HIV). This virus is rapidly spreading throughout the world and is prevalent in various sub-populations, including individuals who receive blood transfusions, individuals who use needles contaminated with the disease, and individuals who contact infected fluids. This disease is also widespread in certain countries. Currently, no known cure exists.

It has long been recognized that a simple, reliable and economically efficient method for reducing the infectivity of the HIV virus is needed to decrease transmission of the disease. Additionally, a method of treating fluids of infected individuals is needed to decrease transmission of the virus to others in contact with these fluids. Furthermore, a method of treating blood given to blood banks is needed to decrease transmission of the virus through individuals receiving transfusions. Moreover, an apparatus and method are needed for decreasing the viral load of an individual or an animal by treating the plasma of that individual and returning the treated plasma to the individual such that the viral load in the plasma is decreased.

Other major viral infections that affect animals and humans include, but are not limited to meningitis, cytomegalovirus, and hepatitis in its various forms. While some forms of hepatitis may be treated with drugs, other forms have not been successfully treated in the past.

At the present time, most anti-viral therapies focus on preventing or inhibiting viral replication by manipulating the initial attachment of the virus to the T4 lymphocyte or macrophage, the transcription of viral RNA to viral DNA and the assemblage of new virus during reproduction. Such a focus has created major difficulty with existing treatments, especially with regard to HIV. Specifically, the high mutation rate of the HIV virus often renders treatments ineffective shortly after application. In addition, many different strains of HIV have already become or are becoming resistant to anti-viral drug therapy. Furthermore, during anti-viral therapy, resistant strains of the virus may evolve. Finally, many common therapies for HIV infection involve several undesirable side effects and require patients to ingest numerous pills daily. Unfortunately, many individuals are afflicted with multiple infections caused by more than one infectious agent, such as HIV, hepatitis and tuberculosis. Such individuals require even more aggressive and expensive drugs to counteract disease progression. Such drugs may cause numerous side effects as well as multi-drug resistance.

Therefore, an effective method and apparatus is needed that does not rely on drugs for combating infectious organisms found in fluids.

Thus, a need exists to overcome the deficiencies of conventional systems and methods for removing lipids from fluids, such as plasma or serum, and for removing lipids from infectious organisms contained in a fluid. Furthermore, a need exists for a medical apparatus and method to perform delipidation rapidly, either in a continuous or discontinuous manner of operation. A need further exists for such an apparatus and process to perform safely and reliably, and to produce delipidated fluid having residual plasma solvent levels meeting acceptable standards. In addition, a need exists for an apparatus having minimal physical connection between a patient and the lipid apheresis process. Furthermore, a need exists for an economical medical apparatus that is sterile and made of a disposable construction for a single use application. Finally, a need exists for such an apparatus and process to be automated, thereby requiring minimal operator intervention during the course of normal operation.

SUMMARY OF THE INVENTION

This invention is directed to systems and methods for removing lipids from a fluid or from lipid-containing organisms, or both, and, more particularly, this invention is directed to the removal of lipids or lipid-containing organisms from fluids using a single solvent. Specifically, these systems are adapted to remove lipids from a fluid or lipid-containing organisms in a fluid, or both, by contacting the fluid with a single solvent in one or more passes through a system.

In one embodiment of this invention, lipids are removed from a fluid containing lipids or from a lipid-containing organism in a two-stage process comprising a first stage and a second stage. In the first stage, a fluid is mixed with an extraction solvent to separate lipids from the fluid or from lipid-containing organisms found in the fluid. In one embodiment, the first stage is conducted by mixing a fluid and an extraction solvent using a mixing device, such as, but not limited to, a homogenizer. In some embodiments, the extraction solvent is a single solvent such as, but not limited to, an ether. However, in other embodiments, the extraction solvent may be other materials as defined below. After the homogenizer has been shut off, the fluid and the solvent are separated via gravity, a centrifuge or other means. Typically, after separation, three layers of materials form, which include a layer of at least partially delipidated fluid that may contain some of the solvent, a layer of free lipids that have been separated from the fluid, and a layer of solvent having dissolved lipids. The partially delipidated fluid is removed from the homogenizer and is sent to the second stage of the process. The free lipids and solvent containing dissolved lipids are removed and may be discarded or processed to recover lipids.

In the second stage, at least a portion of the solvent contained within the at least partially delipidated fluid is removed so that the at least partially delipidated fluid may be administered to a patient without the patient experiencing undesirable consequences. Most solvents that are used in the first stage of this process have a low boiling point, which enable the solvents to be easily removed from the fluid in the second stage. In one embodiment, the extraction solvent is removed by passing the mixture of fluid and extraction solvent through at least one hollow fiber contactor (HFC) one or more times. In some embodiments, a configuration having more than one HFC coupled together in series or parallel, or any combination thereof, is used. The mixture of fluid and extraction solvent is passed through the lumens of the hollow fibers of the HFCs while a material, such as a gas, including, but not limited to, air or nitrogen; or other material such as mineral oil and the like, is passed through the HFC on the shell side of the lumens, or vice versa. The volatile solvent in the fluid evaporates into the gas. After completing the second stage of the process, the at least partially delipidated fluid is capable of being administered to a patient without the patient experiencing undesirable consequences.

An object of this invention is to withdraw lipids from a fluid or from lipid containing-organisms within a fluid while maintaining the fluid in a condition to be returned to a patient.

An advantage of this invention is that fluid can be processed in a continuous manner and returned to a patient without requiring withdrawal of an unacceptable level of blood from the patient. Furthermore, this invention may be used as a discontinuous or batch system for processing fluid, such as plasma from a blood bank.

Another advantage of this invention is that the concentration of lipids in a fluid or lipids in lipid-containing organisms, or both, may be reduced in a fluid in a time efficient manner.

Yet another advantage of this invention is that portions of these systems that contact a fluid during operation are capable of being produced as disposable members, which reduces the amount of time needed to prepare a system for use by another patient.

These and other features and advantages of the present invention will become apparent after review of the following drawings and detailed description of the disclosed embodiments.

BRIEF DESCRIPTION OF THE DRAWINGS

FIG. 17 is a schematic diagram of a recirculating embodiment of a second stage of this invention.

DETAILED DESCRIPTION OF THE INVENTION

Figure 1:
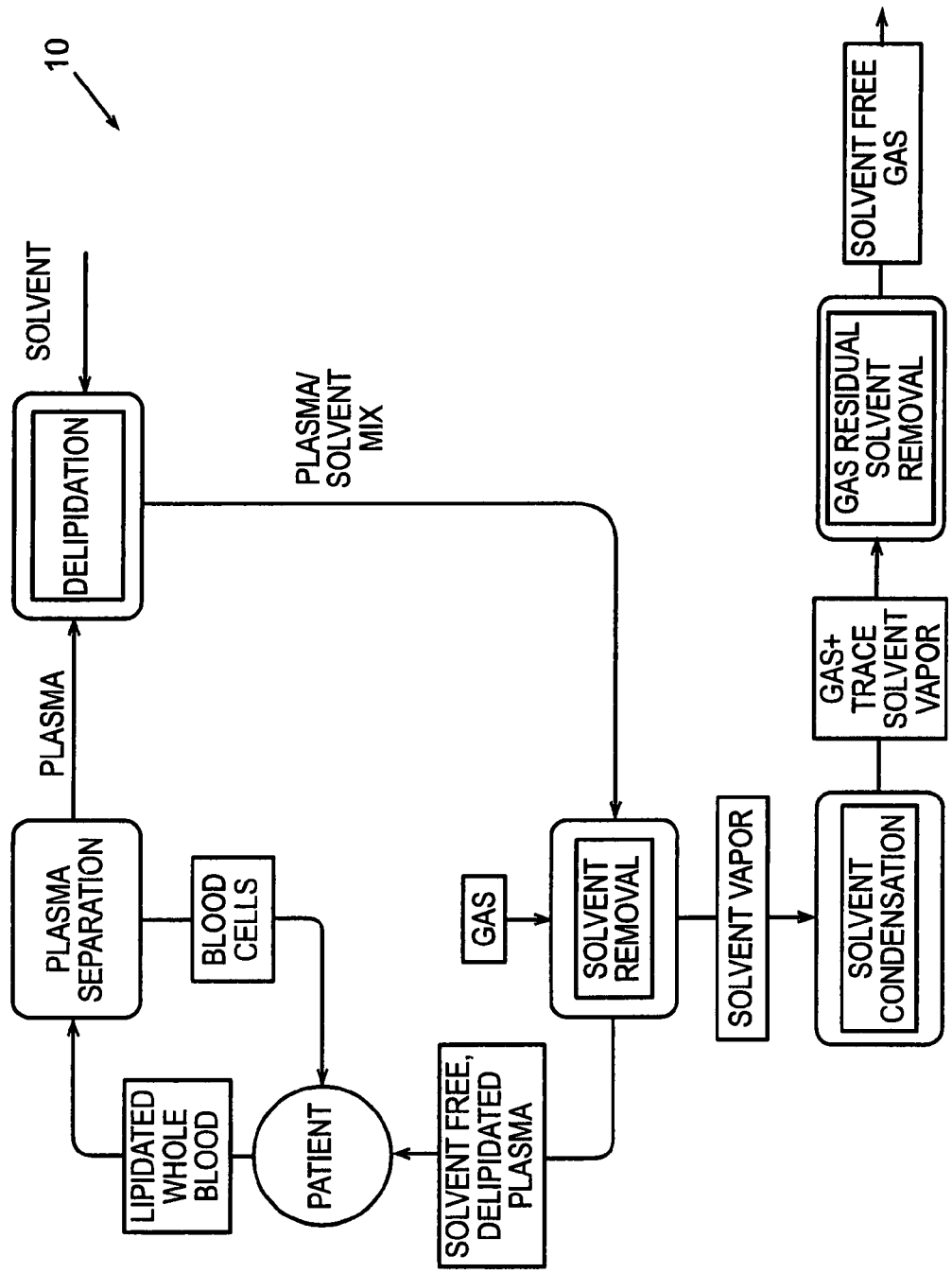
FIG. 1 is a block diagram of a delipidation method of this invention.

This invention relates to systems, apparatuses and methods useful for delipidation of fluids in animals, including humans. These systems and apparatuses can treat arteriosclerosis and atherosclerotic vascular diseases by removing lipids from blood of animals and humans. These systems and apparatuses can treat infectious disease by removing lipid from lipid-containing organisms or infectious agents circulating within the blood of animals and humans, thereby rendering the organisms less infective. These systems are capable of treating fluid, which may be plasma from humans or animals or any other fluid listed below.

I. Definitions and Solvents

A. Definitions

The term "fluid" is defined as fluids from animals or humans that contain lipids, fluids from culturing tissues and cells that contain lipids, fluids mixed with lipid-containing cells, and fluids mixed with lipid-containing organisms. For purposes of this invention, delipidation of fluids includes delipidation of cells and organisms in a fluid. Fluids include, but are not limited to: biological fluids; such as; blood; plasma; serum; lymphatic fluid; cerebrospinal fluid; peritoneal fluid; pleural fluid; pericardial fluid; various fluids of the reproductive system including, but not limited to, semen, ejaculatory fluids, follicular fluid and amniotic fluid; cell culture reagents such as normal sera, fetal calf serum or serum derived from any animal or human; and immunological reagents, such as various preparations of antibodies and cytokines from culturing tissues and cells, fluids mixed with lipid-containing cells, and fluids containing lipid-containing organisms, such as a saline solution containing lipid-containing organisms.

The term "hollow fiber contactor" (HFC) is defined as being any conventional HFC or other HFC. Typically, HFCs have an outer body, referred to as a shell and forming a chamber, for containing a plurality of hollow fibers positioned generally parallel to a longitudinal axis of the shell. The hollow fibers are generally cylindrical tubes having small diameters formed by a permeable membrane having pores that allow certain materials pass through the membrane. The HFC is designed to allow a first material to pass through the lumens of the hollow fibers and a second material to pass through the HFC on the shell side of the hollow fibers. The first material may pass from the lumens of the hollow fibers, through the pores of the hollow fibers and into the second material on the shell side of the hollow fibers, or vice versa. The ability for the materials to pass through the pores of the hollow fibers is predicated on numerous factors, such as pore size, pressure, flow rate, solubility, and others.

The term "lipid" is defined as any one or more of a group of fats or fat-like substances occurring in humans or animals. The fats or fat-like substances are characterized by their insolubility in water and solubility in organic solvents. The term "lipid" is known to those of ordinary skill in the art and includes, but is not limited to, complex lipid, simple lipid, triglycerides, fatty acids, glycerophospholipids (phospholipids), true fats such as esters of fatty acids, glycerol, cerebrosides, waxes, and sterols such as cholesterol and ergosterol.

The term "lipid" is also defined as including lipid-containing organisms including lipid-containing infectious agents. Lipid-containing infectious agents are defined as any infectious organism or infectious agent containing lipids. Such lipids may be found, for example, in a bacterial cell wall or viral envelope. Lipid-containing organisms include but are not limited to eukaroyotic and prokaryotic organisms, bacteria, viruses, protozoa, mold, fungi, and other lipid-containing parasites.

The term "infectious organism" means any lipid-containing infectious organism capable of causing infection. Some infectious organisms include bacteria, viruses, protozoa, parasites, fungi and mold. Some bacteria which may be treated with the method of this invention include, but are not limited to the following: *Staphylococcus; Streptococcus*, including *S. pyogenes; Enterococci; Bacillus*, including *Bacillus anthracis*, and *Lactobacillus; Listeria; Corynebacterium diphtheriae; Gardnerella* including *G. vaginalis; Nocardia; Streptomyces; Thermoactinomyces vulgaris; Treponema; Camplyobacter; Pseudomonas* including *P.aeruginosa; Legionella; Neisseria* including *N. gonorrhoeae* and *N. meningitides; Flavobacterium* including *F. meningosepticum* and *F. odoratum; Brucella; Bordetella* including *B. pertussis* and *B. bronchiseptica; Escherichia* including *E. Coli; Klebsiella; Enterobacter; Serratia* including *S. marcescens* and *S. liquefaciens; Edwardsiella; Proteus* including *P. mirabilis* and *P. vulgaris; Streptobacillus; Rickettsiaceae* including *R. rickettsii; Chlamydia* including *C. psittaci* and *C. trachomatis; Mycobacterium* including *M. tuberculosis, M. intracellulare, M. fortuitum, M. laprae, M. avium, M. bovis, M. africanum, M. kansasii, M. intracellulare*, and *M. lepraemurium*; and *Nocardia*, and any other bacteria containing lipid in their membranes.

Viral infectious organisms which may be inactivated by the above system include, but are not limited to the lipid-containing viruses of the following genuses: *Alphavirus* (alphaviruses),*Rubivurus* (rubella virus), *Flavivirus* (Flaviviruses), *Pestivirus* (mucosal disease viruses), (unnamed, hepatitis C virus), *Coronavirus*, (Coronaviruses), *Torovirus*, (toroviruses), *Arteivirus*, (arteriviruses), *Paramyxovirus*, (Paramyxoviruses), *Rubulavirus* (Rubulavirus), *Morbillivirus* (morbillivuruses), *Pneumovirinae* (the pneumoviruses), *Pneumovirus* (pneumoviruses), *Vesiculovirus* (Vesiculovirus), *Lyssavirus* (lyssaviruses), *Ephemerovirus* (ephemeroviruses), *Cytorhabdovirus* (plant rhabdovirus group A), *Nucleorhabdovirus* (plant rhabdovirus group B), *Filovirus* (filoviruses), *Influenzavirus A, B* (influenza A and B viruses), *Influenza virus C* (influenza C virus), (unnamed, Thogoto-like viruses), *Bunyavirus* (bunyaviruses), *Phlebovirus* (phleboviruses), *Nairovirus* (nairoviruses), *Hantavirus* (hantaviruses), *Tospovirus* (tospoviruses), *Arenavirus* (arenaviruses), unnamed mammalian type B retroviruses, unnamed, mammalian and reptilian type C retroviruses, unnamed type D retroviruses, *Lentivirus* (lentiviruses), *Spumavirus* (spumaviruses), *Orthohepadnavirus* (hepadnaviruses of mammals), *Avihepadnavirus* (hepadnaviruses of birds), *Simplexvirus* (simplexviruses), *Varicellovirus* (varicelloviruses), *Betaherpesvirinae* (the cytomegaloviruses), *Cytomegalovirus* (cytomegaloviruses), *Muromegalovirus* (murine cytomegaloviruses), *Roseolovirus* (human herpes virus 6), *Gammaherpesvirinae* (the lymphocyte-associated herpes viruses), *Lymphocryptovirus* (Epstein-Bar-like viruses), *Rhadinovirus* (saimiri-ateles-like herpes viruses), *Orthopoxvirus* (orthopoxviruses), *Parapoxvirus* (parapoxviruses), *Avipoxvirus* (fowlpox viruses), *Capripoxvirus* (sheeppoxlike viruses), *Leporipoxvirus* (myxomaviruses), *Suipoxvirus* (swine-pox viruses), *Molluscipoxvirus* (molluscum contagiosum viruses), *Yatapoxvirus* (yabapox and tanapox viruses), Unnamed, African swine fever-like viruses, *Iridovirus* (small iridescent insect viruses), *Ranavirus* (front iridoviruses), *Lymphocystivirus* (lymphocystis viruses of fish), *Togaviridae, Flaviviridae, Coronaviridae, Enabdoviridae, Filoviridae, Paramyxoviridae, Orthomyxoviridae, Bunyaviridae, Arenaviridae, Retroviridae, Hepadnaviridae, Herpesviridae, Poxviridae*, and any other lipid-containing virus.

These viruses include the following human and animal pathogens: Ross River virus, fever virus, dengue viruses, Murray Valley encephalitis virus, tick-borne encephalitis viruses (including European and far eastern tick-borne encephalitis viruses, human coronaviruses 229-E and OC43 and others (causing the common cold, upper respiratory tract infection, probably pneumonia and possibly gastroenteritis), human parainfluenza viruses 1 and 3, mumps virus, human parainfluenza viruses 2, 4a and 4b, measles virus, human respiratory syncytial virus, rabies virus, Marburg virus, Ebola virus, influenza A viruses and influenza B viruses, *Arenaviruss*: lymphocytic choriomeningitis (LCM) virus; Lassa virus, human immunodeficiency viruses 1 and 2, or any other immunodeficiency virus, hepatitis A virus, hepatitis B virus, hepatitis C virus, Subfamily: human herpes viruses 1 and 2, herpes virus B, Epstein-Barr virus), (smallpox) virus, cowpox virus, molluscum contagiosum virus.

All protozoa containing lipid, especially in their plasma membranes, are included within the scope of the present invention. Protozoa that may be inactivated by the system and apparatus of the present invention include, but are not limited to, the following lipid-containing protozoa: *Trypanosoma brucei, Trypanosoma gambiense, Trypanosoma cruzi, Leishmania donovani, Leishmania vianni, Leishmania tropica, Giardia lamblia, Giardia intestinalis, Trichomonas vaginalis, Entamoeba histolytica, Entamoeba coli, Entamoeba hartmanni, Naegleria species, Acanthamoeba species, Plasmodium falciparum, Plasmodium vivax, Plasmodium malariae, Plasmodium ovale, Toxoplasma gondii, Cryptosporidium parvum, Cryptosporidium muris, Isospora belli, Cyclospora cayelansis, Balantidium species, Babesia bovis, Babesia, microti, Babesia divergens, Encephalitozoon intestinalis, Pleistophora species, Nosema ocularum, Vittaforma corneae, Septata intestinalis, Enterocytozoon, Dientamoeba fragilis, Blastocystis species, Sarcocystis species, Pneumocystis carinii, Microsporidium africanum, Microsporidium ceylonensis, Eimeria acervulina, Eimeria maxima, Eimeria tenella* and *Neospora caninum*. It is to be understood that the present invention is not limited to the protozoa provided in the list above.

A preferred protozoa treated with the method of the present invention is Coccidia, which includes *Isospora* species, *Cryptosporidium* species, *Cyclospora* species, *Toxoplasma* species, *Sarcocystis* species, *Neospora* species, and *Eimeria* species. These coccidian parasites cause intestinal disease, lymphadenopathy, encephalitis, myocarditis, and pneumonitis.

The terms "protozoal infection" or "infectious disease" mean diseases caused by protozoal infectious organisms. The diseases include, but are not limited to, African sleeping sickness, Chagas' disease, Leishmaniasis, Giardiasis, Trichomoniasis, amebiasis, primary amebic encephalitis, granulomatous amebic encephalitis, malaria, Toxoplasmosis, Cryptosporidiosis, Isosporiasis, Cyclosporiasis, Balantidiasis, Babesiosis, microsporidiosis, *Dientamoeba fragilis* infection, Blastocystis hominis infection, Sarcosporidiosis, pneumonia, and coccidiosis. A preferred protozoal infection treated with the method of the present invention is Coccidiosis, which is caused by *Isospora* species, *Cryptosporidium* species, *Cyclospora* species, *Toxoplasma* species, *Sarcocystis* species, *Neospora* species, and *Eimeria* species. These coccidian parasites cause human intestinal disease, lymphadenopathy, encephalitis, myocarditis, and pneumonitis. These coccidian parasites also cause disease in animals, including cattle, dogs, cats, and birds. Avians, and chickens, turkeys and quail in particular, are affected by Coccidiosis, especially by *Eimeria* species such as *E. acervulina, E. maxima, E. necatrix, E. bruneti, E. mitis, E. praecox* and *E. tenella*.

The term "continuous" refers to the process of delipidating a fluid, such as plasma, while the animal or human remains connected to an apparatus for delipidating the fluid. Additionally, "continuous" refers to the internal process of the lipid removal system, wherein the fluid continually flows within the lipid removal system from subsystem to subsystem.

The term "batch" refers to the process of delipidating a fluid, such as plasma, without returning or passing the delipidated fluid directly to the animal or human during the delipidation process. Rather, the delipidated fluid is stored. Additionally, "batch" refers to the internal process of the lipid removal machine, wherein the fluid does not continually flow within the lipid removal system from subsystem to subsystem.

The term "delipidation" refers to the process of removing lipids from a fluid or from a lipid-containing organisms.

The term "extraction solvent" is defined as one or more solvents used in the initial stage subsystem of extracting lipids from a fluid. This solvent will enter the fluid and remain in the fluid until removed by other subsystems. Suitable extraction solvents include solvents that extract or dissolve lipid, including but not limited to phenols, hydrocarbons, amines, ethers, esters, halohydrocarbons, halocarbons, and combinations thereof. Preferred extraction solvents are ethers, esters, halohydrocarbons, or halocarbons which include, but are not limited to di-isopropyl (DiPE), which is also referred to as isopropyl ether, diethyl ether (DEE), which is also referred to as ethyl ether, ethyl acetate, dichloromethane, chloroform, isoflurane, sevoflourane, perfluorocyclohexanes, trifluoroethane, cyclofluorohexanol, and combinations thereof.

The term "patient" refers to animals and humans, which may be either a fluid source or a recipient of delipidated fluid or delipidated organisms.

B. Solvents

Numerous organic solvents may be used in the method of this invention for removal of lipid from fluids and from lipid-containing organisms, especially infectious organisms, provided that the solvents are effective in solubilizing lipids. Suitable solvents comprise mixtures of aromatic, aliphatic, or alicyclic hydrocarbons, ethers, phenols, esters, halohydrocarbons, and halocarbons. Preferred solvents are ethers. Asymmetrical ethers and halogenated ethers may be used. It is preferred that the solvent has a relatively low boiling point to facilitate removal via a combination of vacuum and possibly heat applications.

Ethers, used alone, at 100 percent concentration, are the preferred solvent for use in the method of the present invention. Particularly preferred are the $C_4$-$C_8$ containing-ethers, including but not limited to, diethyl ether, and propyl ethers, including but not limited to di-isopropyl ether. Also useful in the present invention are combinations of ethers, such as di-isopropyl ether and diethyl ether. In one embodiment, lipid is removed from the viral envelope or bacterial cell wall of the infectious organism.

Hydrocarbons in their liquid form dissolve compounds of low polarity such as the lipids in fluids and lipids found in membranes of organisms. Hydrocarbons which are liquid at about 37° C. are effective in disrupting a lipid membrane of an infectious organism. Accordingly, hydrocarbons comprise any substantially water immiscible hydrocarbon which is liquid at about 37° C. Suitable hydrocarbons include, but are not limited to the following: $C_5$ to $C_{20}$ aliphatic hydrocarbons such as petroleum ether, hexane, heptane, and octane; haloaliphatic hydrocarbons such as chloroform, 1,1,2-trichloro-1,2,2-trifluoroethane, 1,1,1-trichloroethane, trichloroethylene, tetrachloroethylene dichloromethane and carbon tetrachloride; thioaliphatic hydrocarbons; perfluorocarbons, such as perfluorocyclohexane, perfluoromethylcyclohexane, and perfluorodimethylcyclohexane; fluroethers such as sevoflurane; each of which may be linear, branched or cyclic, saturated or unsaturated; aromatic hydrocarbons such as benzene; alkylarenes such as toluene, haloarenes, haloalkylarenes and thioarenes. Other suitable solvents may also include: saturated or unsaturated heterocyclic compounds such as water insoluble derivatives of pyridine and aliphatic, thio or halo derivatives thereof; and perfluorooctyl bromide. Another suitable solvent is perfluorodecalin.

II. Introduction

For purposes of explanation, the removal of lipids from plasma, termed delipidation, is discussed here in detail. However, this is not meant to limit the application of the invention solely to delipidation of plasma. Rather, the same principles and process may be applied to other fluids and to removal of lipids from lipid-containing organisms. The delipidation system 10 of this invention is capable of removing at least a portion of a total concentration of lipids from a fluid or lipid-containing organisms in a fluid. In one embodiment, as shown schematically in FIG. 1, delipidation system 10 receives fluid from a patient, or other source, removes lipids contained in the fluid, and returns the delipidated fluid to the patient, or other source. The delipidation system 10 of this invention may be used as a continuous system, by returning fluid to a patient immediately after lipids have been removed or as a batch system, which removes lipids from a fluid but does not return the fluids immediately to the patient. Instead, the processed fluid can be stored and administered at a later time.

In general, delipidation system 10 is comprised of various combinations of subsystems that perform the first and second stages of a delipidation method. The first stage includes separating lipids from a fluid or lipid-containing organisms using an extraction solvent and may be conducted using an initial stage subsystem. The extraction solvent is mixed with a fluid using various methods. In one embodiment, the extraction solvent is mixed using a homogenizer. In some embodiments, the extraction solvent is composed of a single solvent. The second stage includes removal of the extraction solvent from the fluid so that the concentration of solvents in the fluid allows the fluid to be administered to a patient without the patient experiencing undesirable consequences. In one embodiment, the extraction solvent is removed without the use of another solvent. The second stage may be conducted using a second stage subsystem, as described below.

This process is shown schematically in FIG. 1 as being adapted to remove lipids or liquid containing organisms, or both, from plasma taken from human blood. For instance, whole blood is drawn from a patient using conventional procedures and is subjected to a conventional plasma separation process using, for instance, cellular separation systems that may be composed of, but are not limited to, apheresis and plasmapheresis systems, such as SPECTRA and TRIMA manufactured by Cobe BCT, Gambro BCT, Lakewood, Colo.; AUTOPHERESIS-C manufactured by Baxter Healthcare Corporation, Deerfield, Ill.; or AS104 manufactured by Fresenius, Berlin, Germany. In another embodiment, blood is combined with an anticoagulant, such as sodium citrate, and centrifuged at forces approximately equal to 2,000 times gravity. The red blood cells are then aspirated from the plasma. The plasma separation process collects plasma and returns the blood cells to the patient. The plasma is then subjected to the lipid removal process of this invention, which is described in detail below.

III. Delipidation System

As discussed above, the delipidation system 10 may be composed of numerous configurations. Set forth below are numerous embodiments formed from different components that are capable of achieving the objective and advantages described above. These embodiments are described to teach the invention and are not meant to limit the scope of the invention. Rather, each embodiment is but one of many possible configurations that can be used to accomplish the objectives described above.

Suitable materials for use in any of the apparatus components as described herein include materials that are biocompatible, approved for medical applications that involve contact with internal body fluids, and in compliance with U.S. PV1 or ISO 10993 standards. Further, the materials should not substantially degrade, from for instance, exposure to the solvents used in the present invention, during at least a single use. The materials should typically be sterilizable either by radiation or ethylene oxide (EtO) sterilization. Such suitable materials should be capable of being formed into objects using conventional processes, such as, but not limited to, extrusion, injection molding and others. Materials meeting these requirements include, but are not limited to, nylon, polypropylene, polycarbonate, acrylic, polysulphone, polyvinylidene fluoride (PVDF), fluoroelastomers such as VITON, available from DuPont Dow Elastomers L. L. C., thermoplastic elastomers such as SANTOPRENE, available from Monsanto, polyurethane, polyvinyl chloride (PVC), polytetrafluoroethylene (PTFE), polyphenylene ether (PFE), perfluoroalkoxy copolymer (PFA), which is available as TEFLON PFA. from E. I. du Pont de Nemours and Company, and combinations thereof.

The valves used in each embodiment may be composed of, but are not limited to, pinch, globe, ball, gate or other conventional valves. Thus, the invention is not limited to a valve having a particular style. Further, the components of each system described below may be physically coupled together or coupled together using conduits that may be composed of flexible or rigid pipe, tubing or other such devices known to those of ordinary skill in the art.

1. First Stage Subsystem

Figure 2:
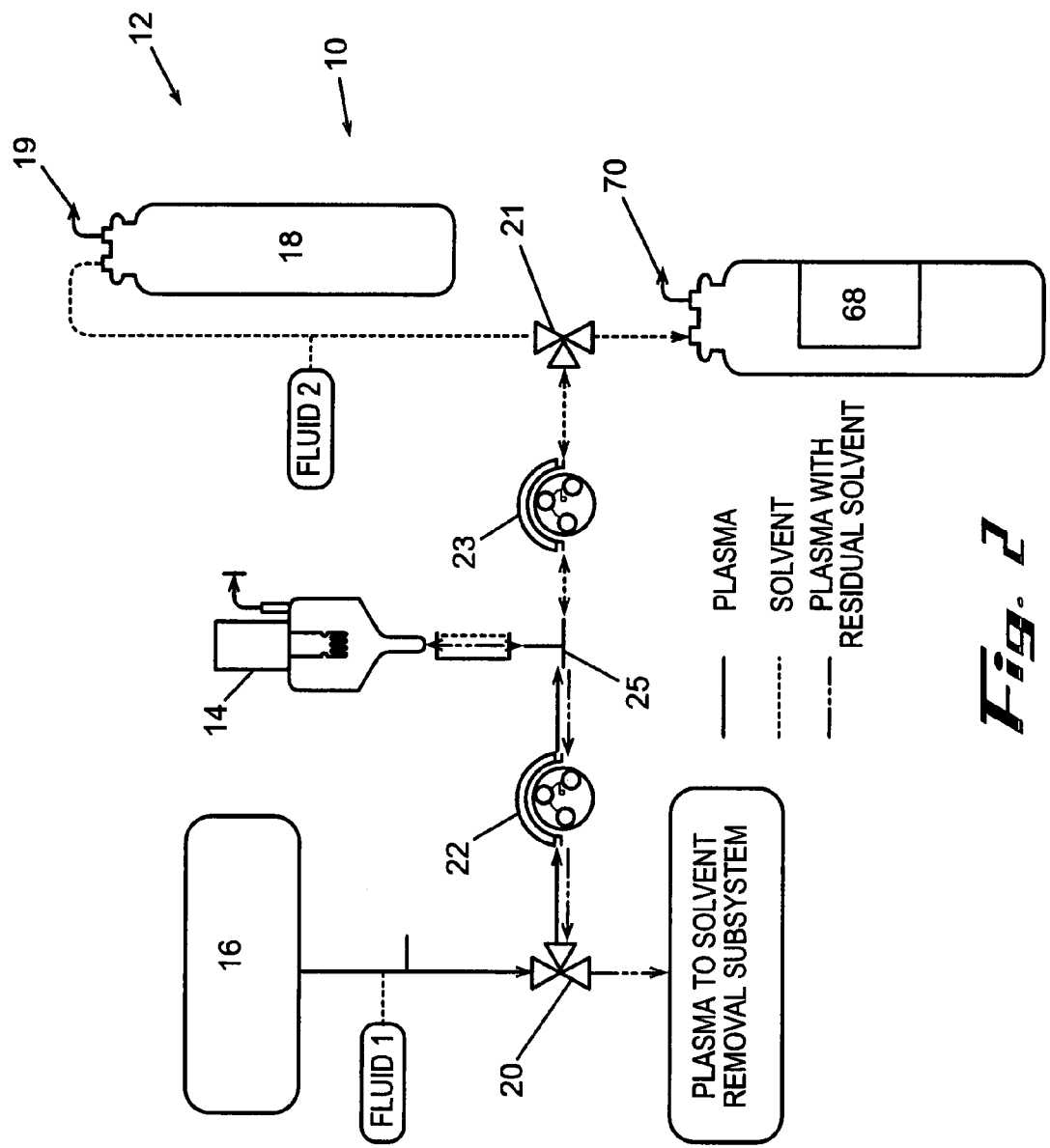
FIG. 2 is a schematic diagram of an embodiment of this invention showing a first stage subsystem.
Figure 3:
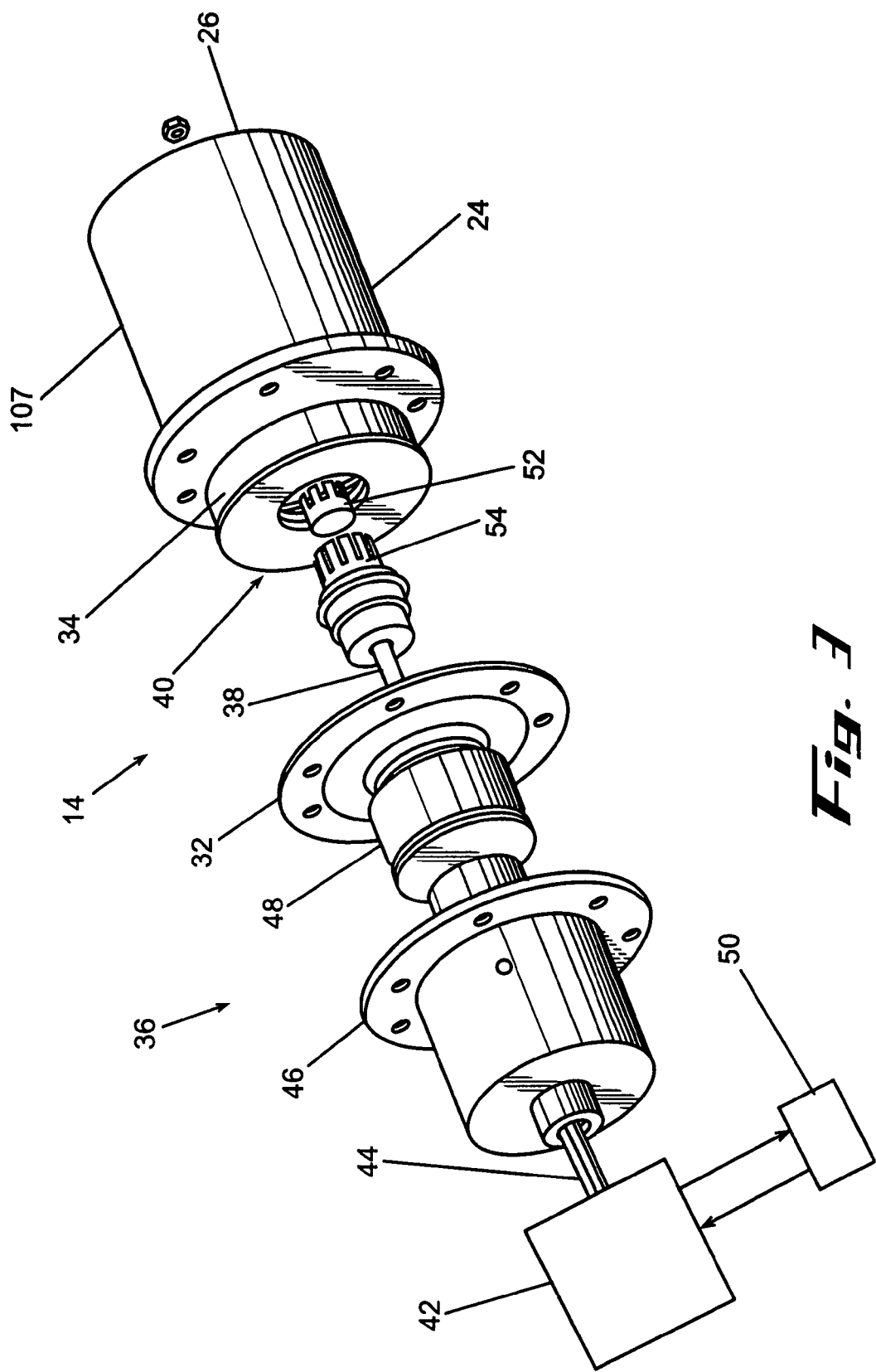
FIG. 3 is an exploded perspective view of the homogenizer identified in FIG. 2.

According to one embodiment of this invention, as shown in FIG. 2, a first stage subsystem 12 includes a delipidation device 14 for removing at least a portion of a total concentration of lipids from a fluid or from a lipid-containing organism. The delipidation device 14 receives a fluid from a fluid source 16 and receives an extraction solvent from an extraction solvent source 18. First stage subsystem 12 may be configured so that the fluid source 16 is a patient, a container, such as a flask, or other such device, or other source. Extraction solvent source 18 is not limited to any device, but may be composed of flasks or other containers capable of safely storing the extraction solvent. Extraction solvent source 18 may also include a vent 19 for safe operation. The flow of fluid to delipidation device 14 is controlled using valve, 20, and the flow of extraction solvent to delipidation device 14 is controlled using valve 21. During operation of first stage subsystem 12, a fluid and an extraction solvent are sent to delipidation device 14. The fluid may be sent to the delipidation device 14 using gravity or a pump 22, which may be a peristaltic pump, such as MASTERFLEX L/S model number 07523-40 available from Cole Parmer Instrument Company, Vernon Hills, Ill., or other pump not having vanes that contact the fluid being pumped. The solvent may be sent to delipidation device 14 using gravity or a pump 23, which may be a peristaltic pump or other pump. The fluid and the extraction solvent first contact each other at connection 25 and form a first mixture that is sent to delipidation device 14. In another embodiment, the fluid and the extraction solvent may be introduced serially into delipidation device 14 so that they do not contact each other until being introduced into delipidation device 14.

Figure 20:
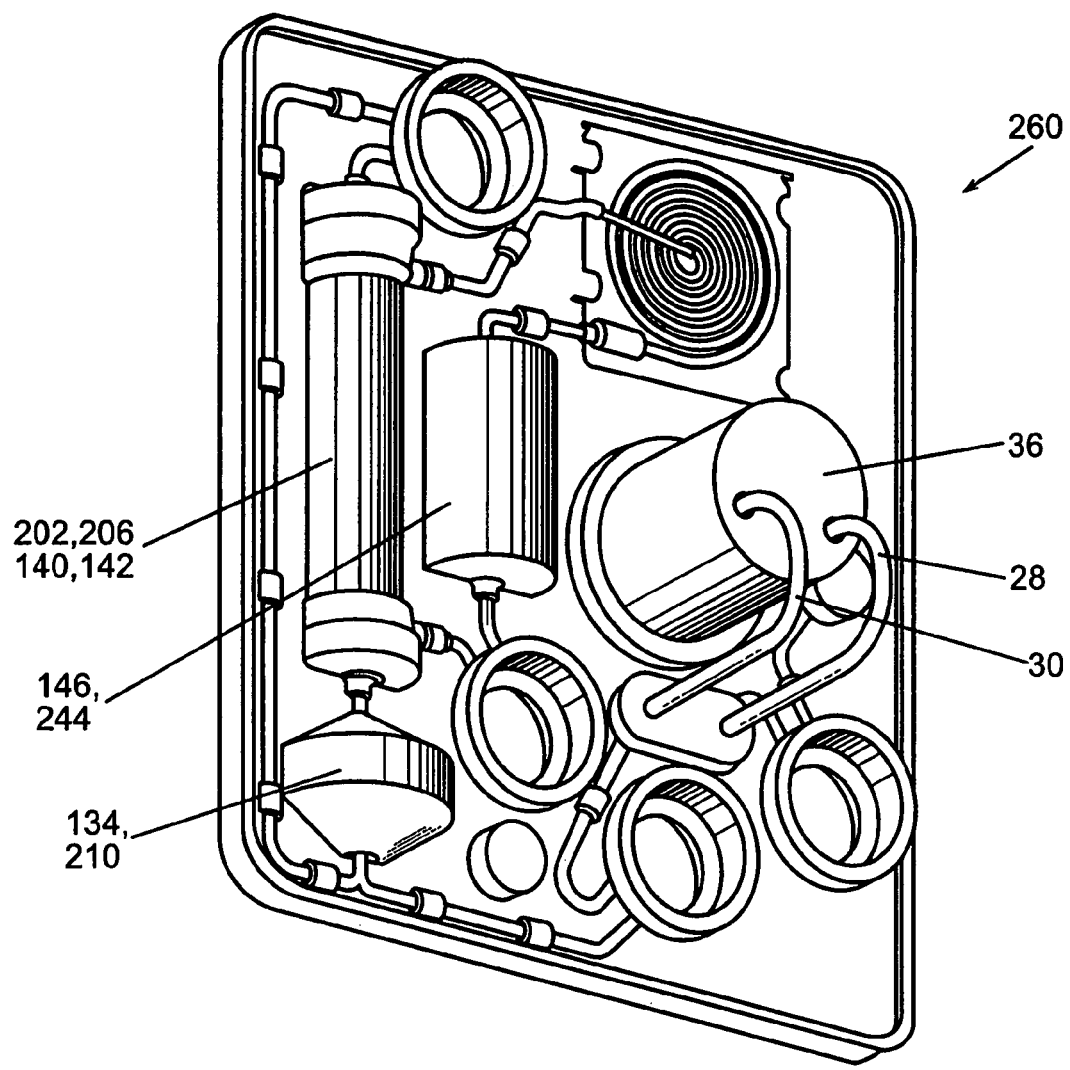
FIG. 20 is a schematicized perspective view of the device of FIG. 2 contained in a module.

Delipidation device 14 may be composed of one or more devices having various configurations. Delipidation device 14 may be any device capable of mixing an extraction solvent with a fluid through the addition of energy, which may be the addition of energy through mechanical agitation or the like. In one embodiment, delipidation device 14 may be a homogenizer 36, as shown in FIGS. 3-6. Homogenizer 36 is composed of a chamber 24 that is a hollow cylinder that may be affixed to a chamber base 26 for receiving a fluid and an extraction solvent. Chamber 24, or chamber base 26, may further include one or more inflow ports 28 and outflow ports 30, as shown in FIG. 20. Inflow port 28 and outflow port 30 provide fluid communication between the interior portions of the chamber 24 and other components of delipidation device 14. Homogenizer 36 may be a reusable unit or a disposable, single-use device. The homogenizer 36 may be operated while positioned vertically, horizontally, or in any other orientation permitted by the orientation of drive shaft 44 of motor 42.

Referring again to FIG. 3, chamber 24 may be enclosed on an end opposite base 26 by an interface plate 32, which may either be permanently or releasably attached to chamber 24 to form a sealed container with fluid ingress limited to inflow port 28 and fluid egress limited to outflow port 30, as shown in FIG. 20. A flow direction insert 34 may be positioned between interface plate 32 and chamber 24. Flow direction insert 34 may provide one or more deflector surfaces, not shown, that minimize or eliminate stagnant pockets of fluid within chamber 24. Flow direction insert 34 minimizes the possibility of having poor homogenization of fluid and solvent in chamber 24.

Homogenizer 36 may also include a drive shaft 38 coupled to a rotor-stator assembly 40. Drive shaft 38 is positioned within chamber 24 and along a longitudinal axis of chamber 24, and rotor-stator assembly 40 is positioned within chamber 24 when assembled. Rotor-stator assembly 40 may include rotor 52 and stator assembly 54. Homogenizer 36 also may include a motor 42 for rotating rotor-stator assembly 40. Motor 42 is coupled to a drive shaft 44 that is capable of rotating drive shaft 38 using a magnetic drive assembly 46. Magnetic drive assembly 46 is positioned proximate to magnets 48, which are coupled to drive shaft 38. In one embodiment, motor 42 may be controlled by a control system 50, such as a computer. Drive motor 42 may also be capable of operating in the range between about 3,000 revolutions per minute (rpm) to about 30,000 rpm, and more specifically, at least about 24,000 rpm.

Figure 4:
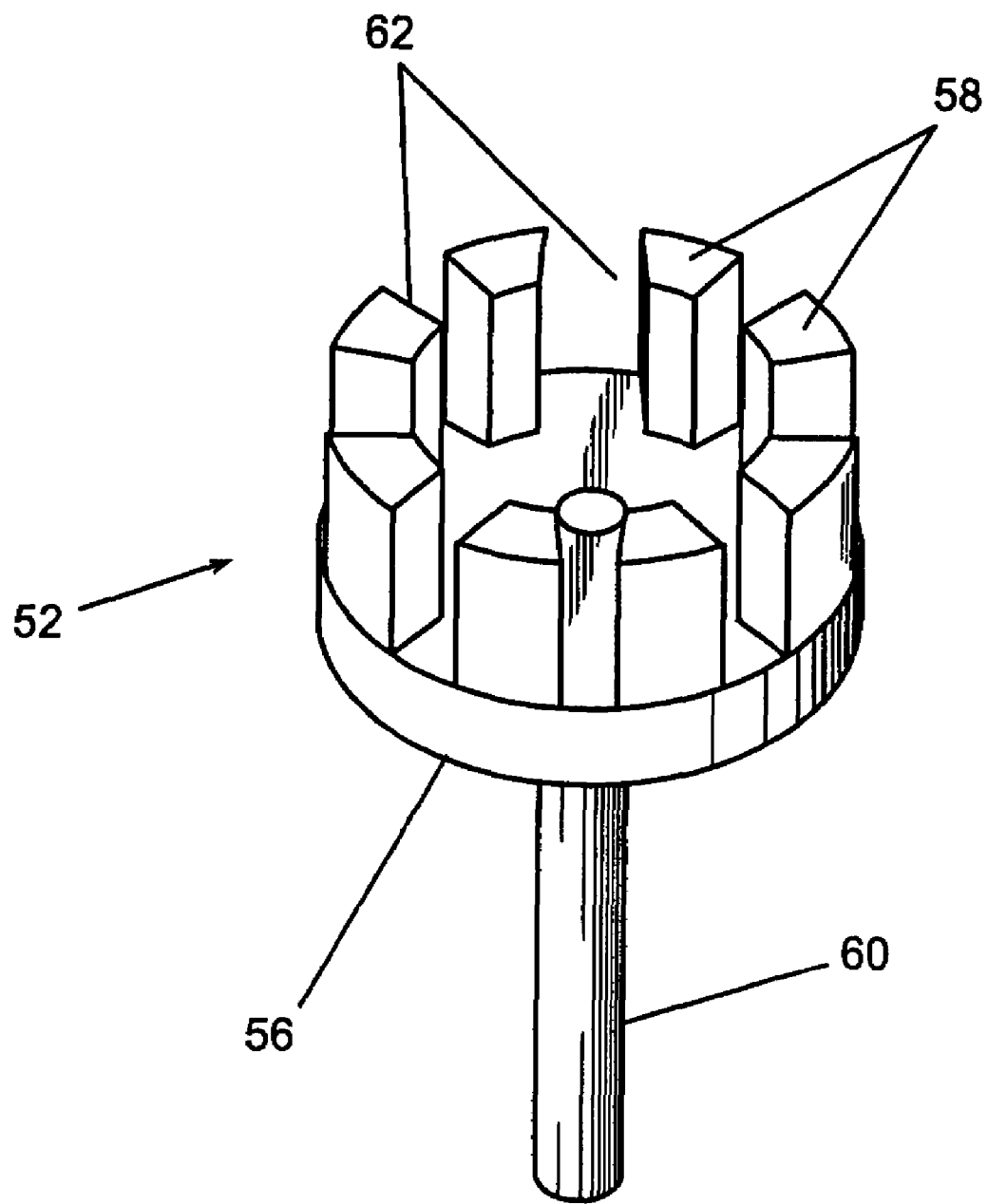
FIG. 4 is a perspective view of a rotor used with the homogenizer shown in FIG. 3.
Figure 5:
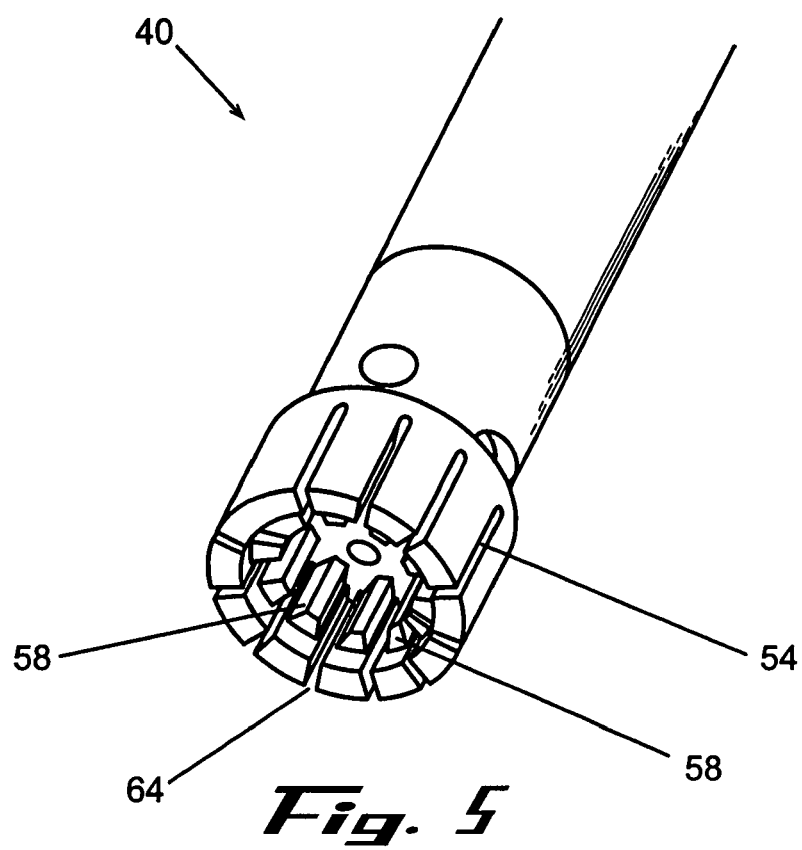
FIG. 5 is a perspective view of the rotor shown in FIG. 4 positioned within a rotor-stator assembly.
Figure 6:
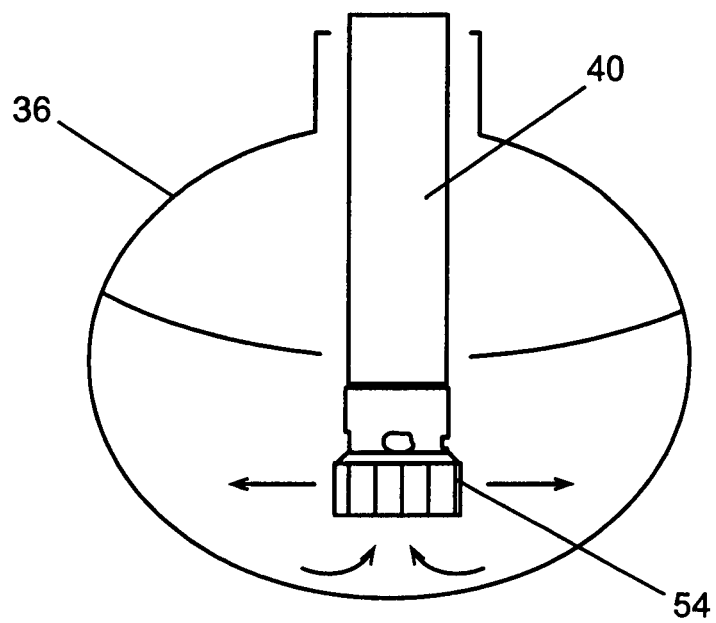
FIG. 6 is a schematic side view of the rotor-stator assembly of FIG. 5 shown in an operating condition.

As shown in FIG. 4, rotor 52 is typically a cylindrical structure including a rotor 52 having a head 56 with two or more teeth 58 extending generally away from the drive shaft 60. Teeth 58 are separated by slots 62 located in the interspaces between adjacent teeth 58. Teeth 58 may be displaced parallel to, or in angulated orientations with respect to, the rotational axis of drive shaft 60. Head 56 and teeth 58 are sized to freely rotate when positioned in stator assembly 54 as shown in FIG. 5.

Stator assembly 54 may be fixed in position either to chamber base 26 or flow direction insert 34. Stator assembly 54 may be configured as shown in FIG. 5 to include a hollow, cylindrical stator body having a series of stator slots 64 that are formed by a plurality of fenestrations within the body of stator assembly 54. Stator assembly 54 is configured to allow rotor 52 to rotate freely when positioned within stator assembly 54.

In one embodiment, as shown in FIG. 2, homogenizer 36 receives a mixture of fluid and solvent from connection 25. Specifically, the mixture is sent into chamber 24 through inflow port 28. In chamber 24, the mixture is subjected to the centrifugal forces produced by the high-speed rotation of rotor 52. Rotor 52 functions as an impeller that draws the mixture towards the rotational axis of rotor 52. The mixture is then thrown away from the axis at high rates of speed, as shown for instance with the arrows in FIG. 6. The mixture is subjected to both the dispersal forces of rotor 52 and stator assembly 54 and to gravitational forces. After the mixture has been mixed by homogenizer 36, at least a portion of the lipids contained within the fluid begin to separate from the fluid. The fluid containing the separated lipids and the solvent are then removed from homogenizer 36 through outflow port 30. The geometry of rotor-stator assembly 40 of homogenizer 36 provides vigorous mixing of the solvent and the fluid and typically generates a fine dispersion of droplets having a diameter between about 5 microns and about 20 microns, which enhances the surface contact between the solvent and the fluid.

After mixing the fluid and the solvent, free lipids are separated from the fluid in various ways, such as, but not limited to, gravity, a centrifuge, or a filter. In embodiments where a centrifuge or gravity is used, three layers are typically formed and consist of a layer of fluid, a layer of free lipids, and a layer of extraction solvent with dissolved lipids. The fluid layer often contains about 1% solvent and is the heaviest layer. The solvent and dissolved lipids are usually the lightest layer, and the layer of free lipids often is located between the layer of fluid and the layer of extraction solvent with dissolved lipids.

Figure 7:
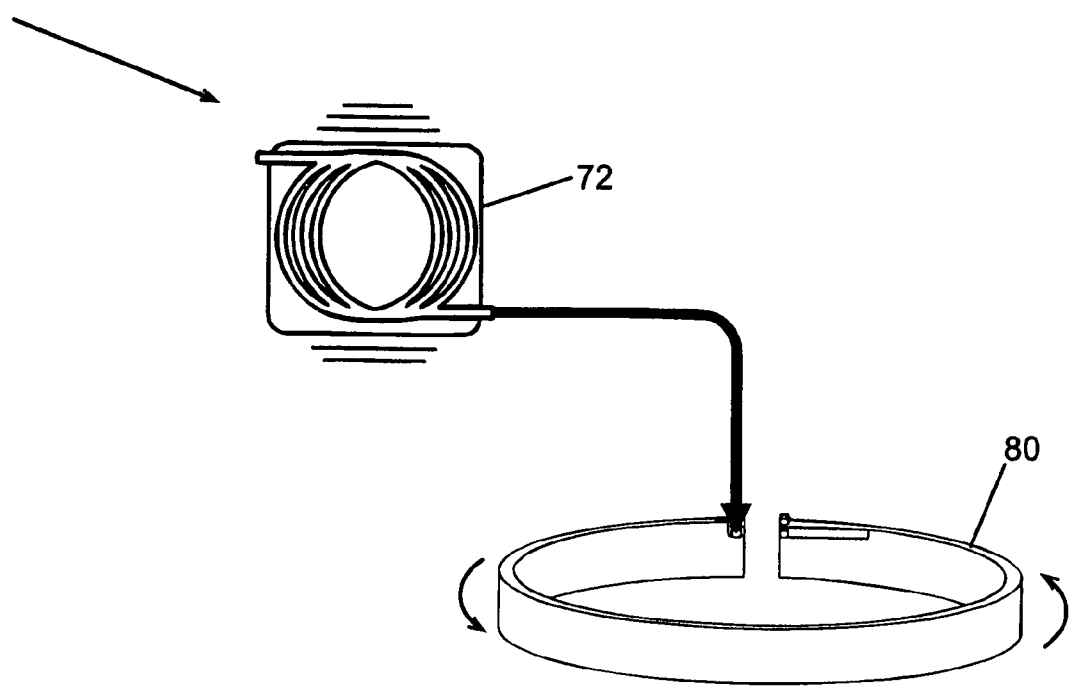
FIG. 7 is a schematic diagram of a delipidation device composed of a vortexer coupled to a centrifuge.

While homogenizer 36 operates at high speeds and forms a mixture of the fluid and a solvent, homogenizer 36 typically does not form an emulsion between the plasma and the extraction solvent because of the vigorous shearing and dispersing action caused by the rotor of homogenizer 36. As a result, the fluid and the extraction solvent are able to separate via gravity within about two to about five minutes after homogenizer 36 has been stopped. If the fluid has a high concentration of cholesterol or the homogenizer forms an emulsion during the mixing process, a centrifuge may used to separate the solvent and the fluid. The centrifuge may be either a batch centrifuge or a continuous centrifuge, as shown in FIG. 7, which operates by receiving the combined fluid and solvent through one port and producing the materials separated through exit ports. The centrifuge is operated for about 30 seconds to about 3 minutes to separate the solvent from the fluid. The fluid and solvent may also be separated using a filter. The filter allows the fluid to pass through the filter while retaining the solvent and free lipids, or vice versa. Suitable filters may have lipophilic or hydrophilic membranes.

Figure 8:
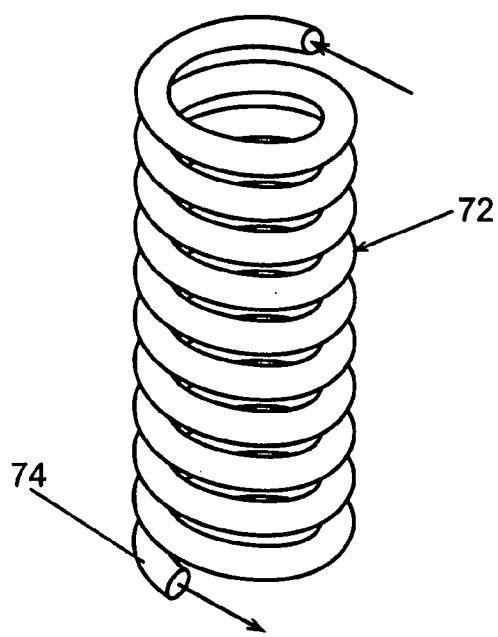
FIG. 8 is a perspective view of a continuous vortexer usable in the delipidation device shown in FIG. 7.
Figure 9:
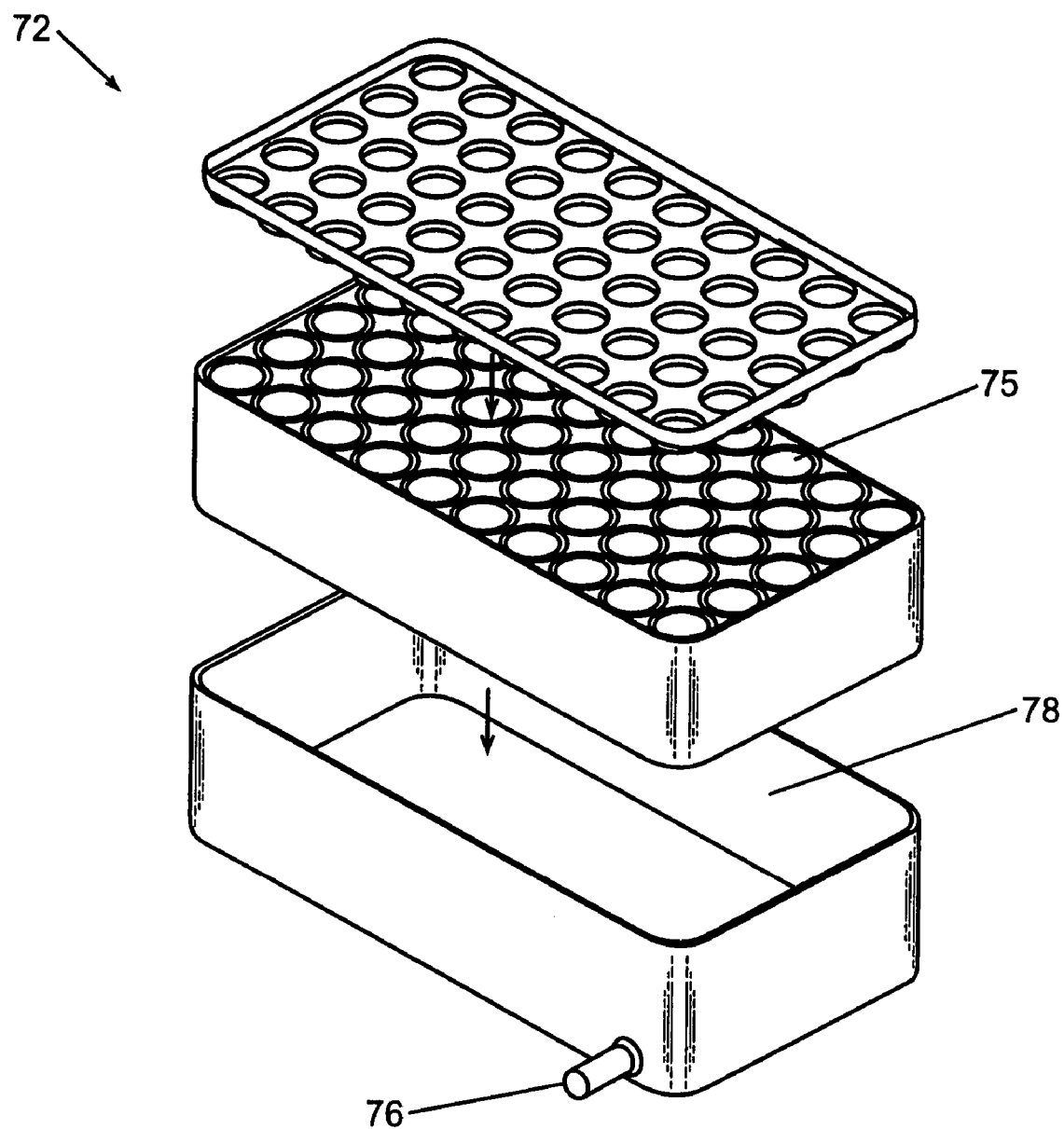
FIG. 9 is a perspective view of a batch vortexer usable in the delipidation device shown in FIG. 7.

According to another embodiment of this invention, delipidation device 14 may be composed of a vortexer 72, as shown schematically in FIG. 7 and in FIGS. 8 and 9. Vortexer 72 may be either a continuous vortexer, as shown in FIG. 8, or a batch vortexer, as shown in FIG. 9. A continuous vortexer 72 mixes fluids as the fluids flow through a cylindrical tube 74 having a spiral or straight configuration. Tube 74 is vibrated using external vibration, which causes a vortex to form within tube 74 while the fluids are flowing through tube 74 in the direction of the arrows shown in FIG. 8.

As shown in FIG. 9, a batch vortexer 72 typically includes a housing 78 for containing an array of tubes or chambers 74 that are filled with a batch of the combined fluid and extraction solvent and are externally vibrated, which creates a vortex in each tube. Inlet port 76 allows housing 78 to be filled with a fluid and solvent. The non-rotating vortexer 72 is advantageous because it is relatively inexpensive to produce, and thus can be incorporated in a disposable design. Furthermore, vortexer 72 does not have any moving parts and requires no bearings or bushings, which makes the device less susceptible to failure. If an emulsion forms, a centrifuge 80, as shown in FIG. 7, may be used to break the emulsion to separate lipids from a fluid and solvent.

The centrifuge 80 shown in FIG. 7 may be used as a delipidation device, either alone or in combination with vortexer 72. Centrifuge 80 may be configured as a discontinuous flow through channel in the shape of a ring that is spun about its axis. During operation, centrifuge 80 receives a mixture of fluid and solvent through one port. After being spun in centrifuge 80 for an appropriate time, such as between 30 seconds to 3 minutes, the mixture of fluid exits the ring as separated fluid and solvent. The spinning motion, as denoted by the arrows adjacent the centrifuge, generates centrifugal forces that separate a fluid from solvent.

Figure 10:
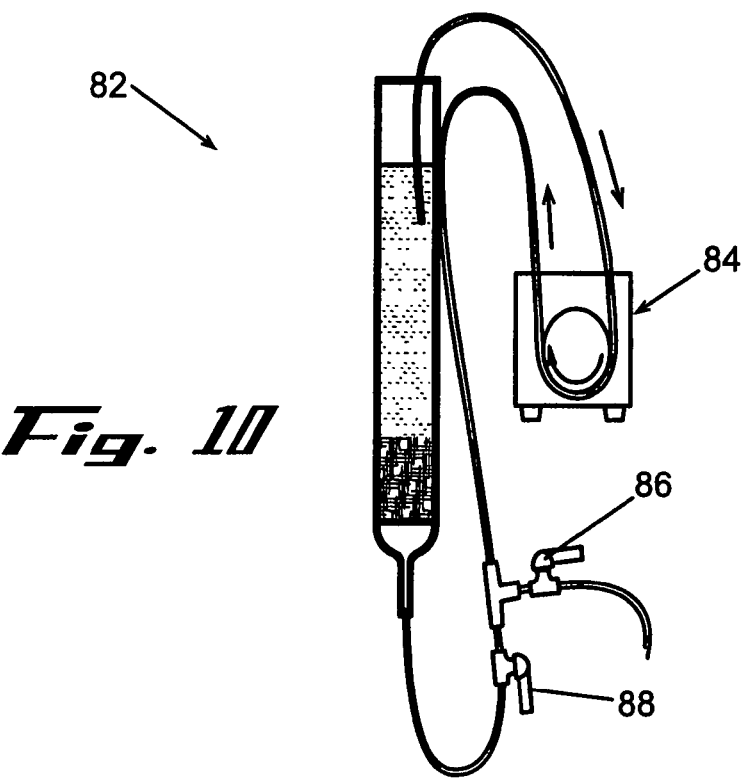
FIG. 10 is schematic diagram of a glass fitt separator usable as a delipidation device.

In another embodiment, delipidation device 14 may be composed of a glass frit disperser or separator 82 as shown in FIG. 10. Glass fitt separator 82 delipidates a fluid by creating a fine dispersion of solvent droplets in the fluid. Solvent droplets are created by pumping solvent, using, for instance, pump 84, through glass frit separator 82 containing a volume of fluid. Initially, the solvent collects on top of the fluid and subsequently forms droplets that are dispersed throughout the fluid. Alternately, the fluid may be pumped into glass frit separator 82 containing a solvent. As shown in FIG. 10, valves 86 and 88 may be used to control the circulation of fluids through glass flit separator 84.

Figure 11:
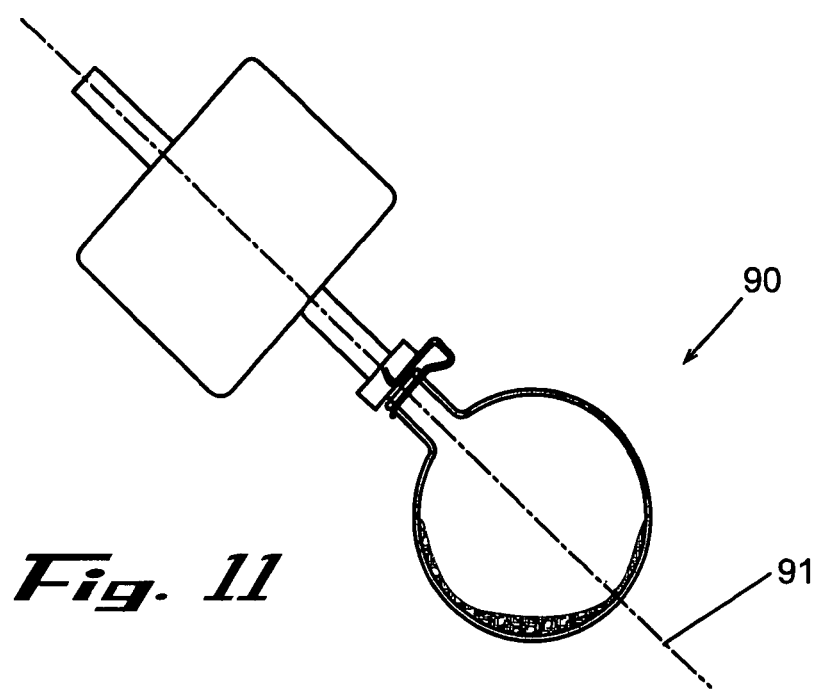
FIG. 11 is schematic diagram of a rotating flask usable as a delipidation device.

FIG. 11 shows a rotating flask 90 usable as a delipidation device 14. Rotating flask 90 rotates around an axis 91, thereby slowly mixing the fluid and a solvent. Typical rotational speeds are approximately 100 rpm, although other speeds may be used to achieve mixing. Delipidation occurs typically by mixing a fluid with a solvent in the rotating flask.

Figure 12:
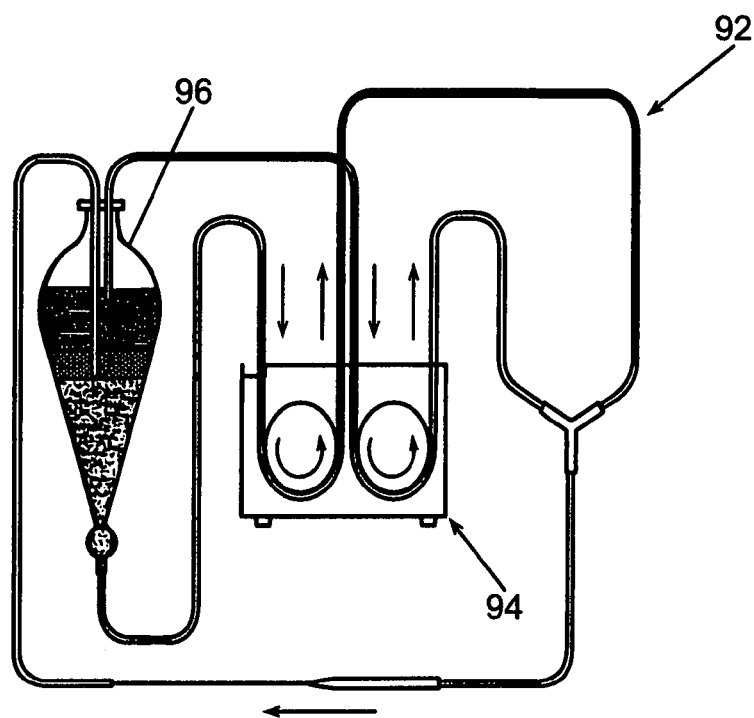
FIG. 12 is schematic diagram of a high shear tube usable as a delipidation device.

FIG. 12 shows a high shear tube 92 usable as a delipidation device 14. High shear tube 92 functions by continuously recirculating a fluid and a solvent using one or more pumps 94 through a small diameter tube, which has a diameter of about 0.032 inches, at a flow rate of approximately 100 milliliters per minute. The shear generated within the tube causes delipidation of the plasma. After delipidation has occurred, the fluid and the solvent typically separate via gravity in chamber 96.

Figure 13:
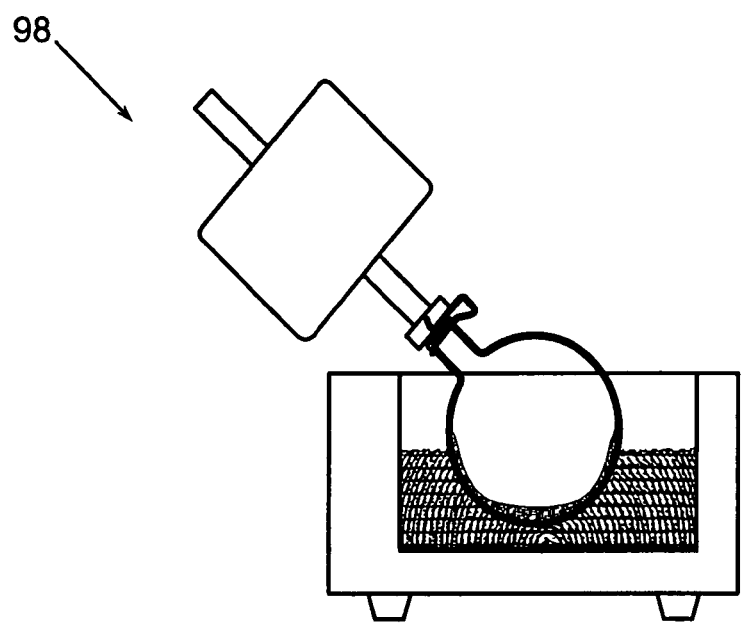
FIG. 13 is schematic diagram of a sonicated flask usable as a delipidation device.

FIG. 13 depicts a sonicated flask 98 usable as a delipidation device 14. Sonicated flask 98 operates by mixing a fluid and a solvent in a flask and immersing the flask in a sonicated bath. The ultrasonic energy imparted through the flask causes lipids to separate from a fluid. In addition, the flask can further be rotated to increase lipid separation. The flask may be formed from various types of materials and shapes. Typically, the flask is made from glass and has a round shape.

Figure 14:
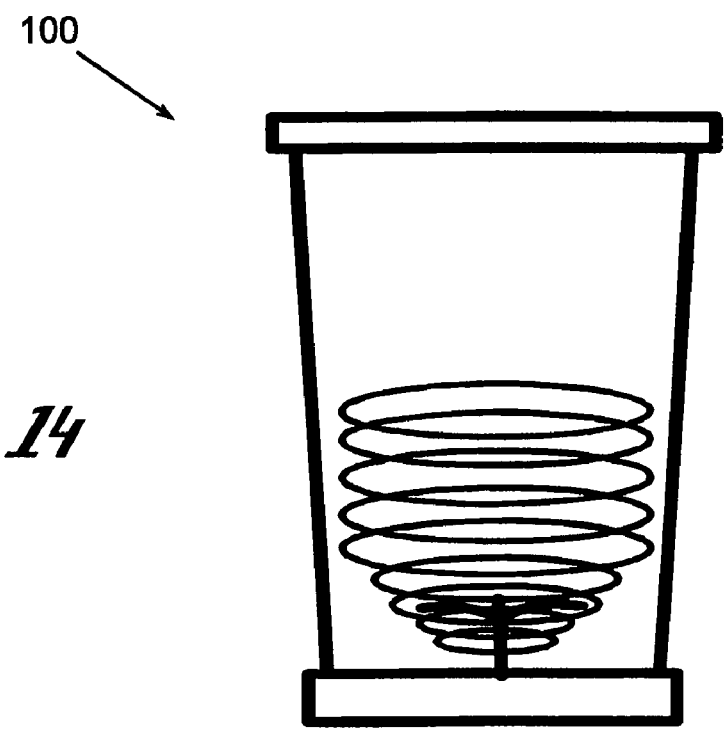
FIG. 14 is schematic diagram of a blender usable as a delipidation device.

FIG. 14 depicts a blender 100 usable as a delipidation device 14. Blender 100 operates by rotating a blending member in blender 100 to blend a solvent and a fluid. In one embodiment, the blending member of a standard laboratory blender may be rotated at a speed of approximately 6,000 rpm. Lipid separation occurs via the shearing action and vortexing of the fluid and the solvent. The delipidated plasma is typically separated via gravity after the fluid and solvent have been mixed in blender 100.

Figure 15:
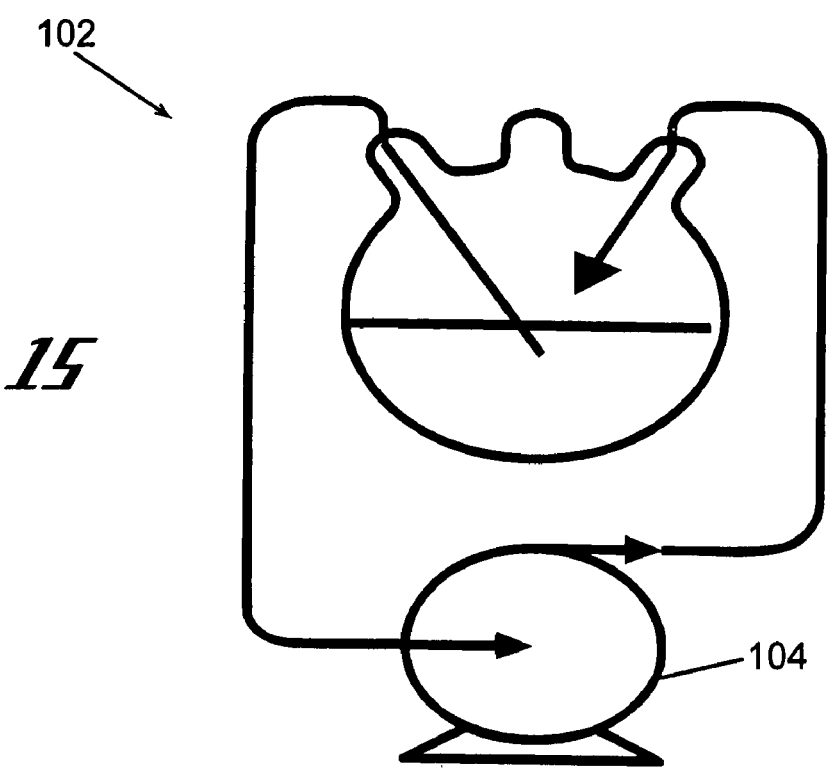
FIG. 15 is schematic diagram of a centrifugal pump usable as a delipidation device.

FIG. 15 depicts a centrifugal pump 102 usable as a delipidation device 14, which functions by recirculating a fluid and an extraction solvent through, for instance, a pump 104. In one embodiment, pump 104 may operate at a speed of approximately 3,000 rpm and generate a circulating flow rate of about 10 liters per minute. Pump 104 may be a magnetically driven pump or other type pump. Delipidation occurs via the fluid flow and the shear created at the pump impeller. The delipidated plasma is then typically separated from the extraction solvent via gravity.

First stage subsystem 12 may be composed of at least one of these delipidation devices to perform the first stage of the delipidation method. In other embodiments of this invention, first stage subsystem 12 may be composed of any combination of these devices or other devices.

2. Second Stage Subsystem

Figure 16:
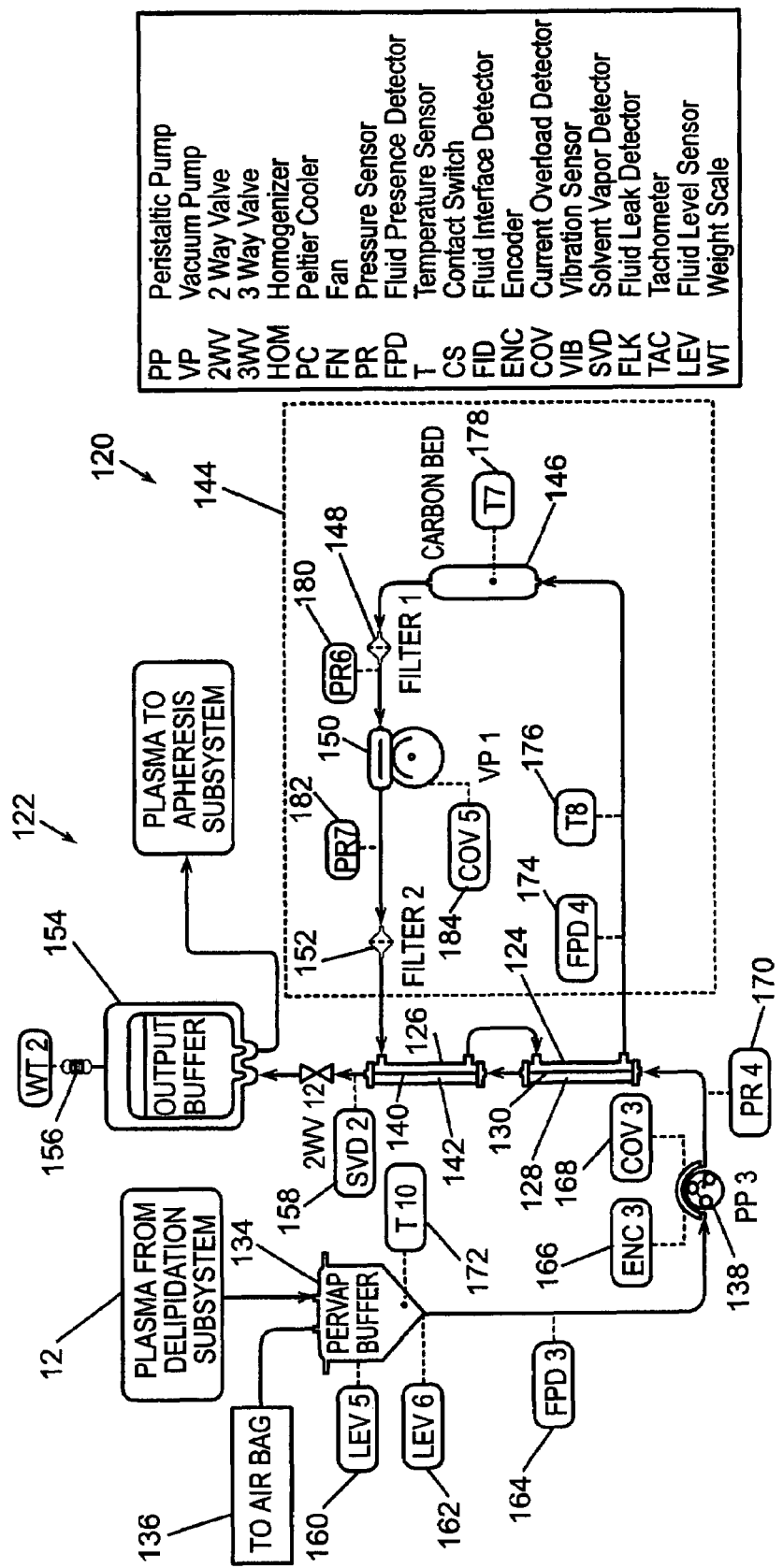
FIG. 16 is a schematic diagram of once-through embodiment of a second stage of this invention.
Figure 11:
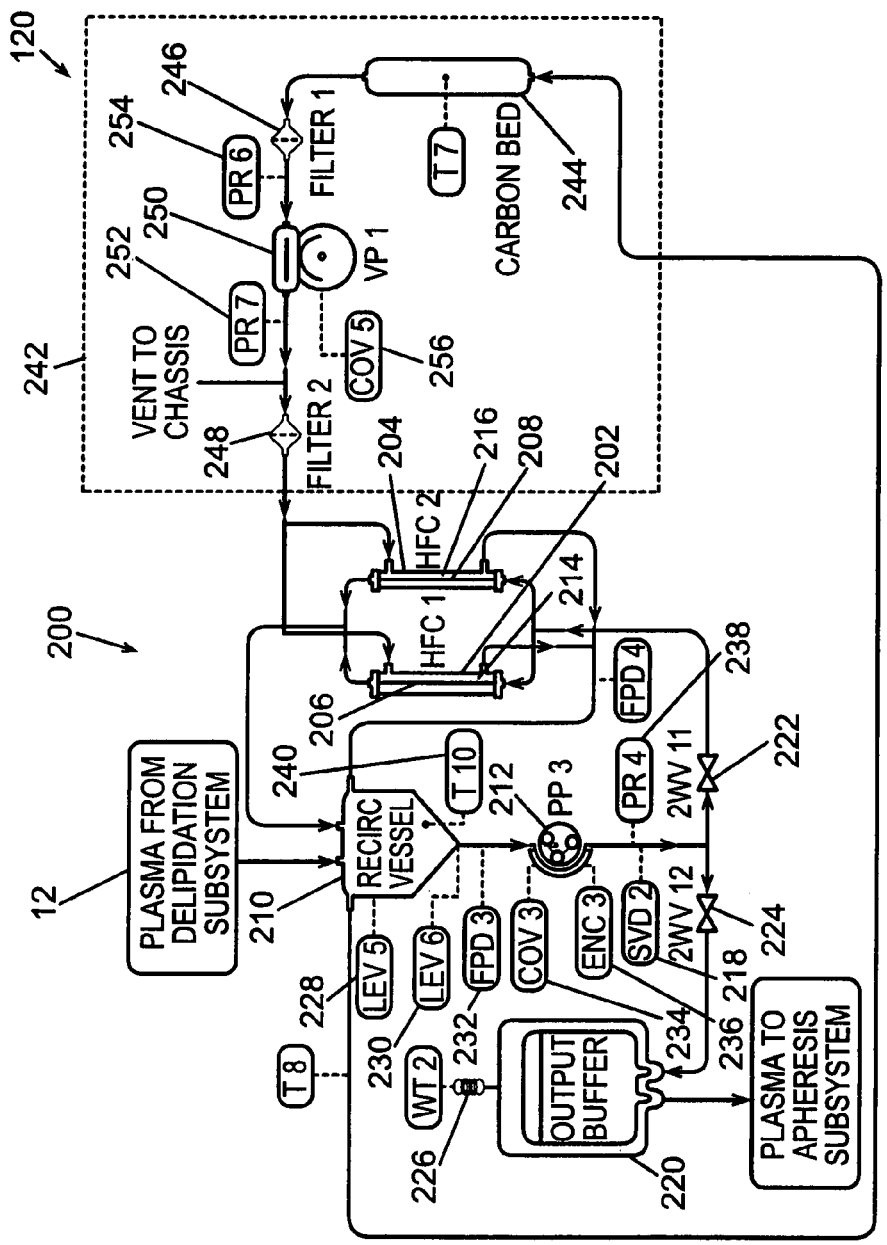

The second stage subsystem 120 removes at least a portion of the extraction solvent from the fluid that was not removed in the first stage subsystem 12 so that the solvent level in the mixture of fluid and solvent is beneath a particular threshold. The second stage subsystem 120 may be composed of at least two embodiments, as shown in FIGS. 16 and 17. Specifically, FIG. 16 shows a once-through subsystem that is capable of removing at least a portion of the extraction solvent from a fluid by passing the mixture of fluid and extraction solvent through the system only one time so that the concentration of the extraction solvent is less than a particular threshold, thereby enabling the fluid to be administered to a patient without the patent experiencing undesirable consequences. FIG. 17 depicts a recirculating subsystem that is also capable of reducing the concentration of the extraction solvent to a level beneath a particular threshold. However, the solvent concentration is reduced to an adequate level by passing the mixture through the recirculating subsystem one or more times. Each of these embodiments is discussed in more detail below.

(a) Once-through Solvent Removal Subsystem

The once-through subsystem 122 depicted in FIG. 16 is composed of two HFCs 124 and 126 for removing an extraction solvent from a fluid. This invention is not limited to a configuration having two HFCs. Rather, once-through subsystem 122 may be composed of any number of HFCs depending on the flow rate of fluids or gases through the lumens of the hollow fibers and through the shell side of the hollow fibers of the HFC, the porosity of the hollow fibers, the pore size, and the amount of surface area of the hollow fiber membrane, and the vapor pressure or the Henry's Law constant for the solvent. Adjusting any one of these factors requires the other factors be changed in order to yield the same output at the same rate.

Figure 18:
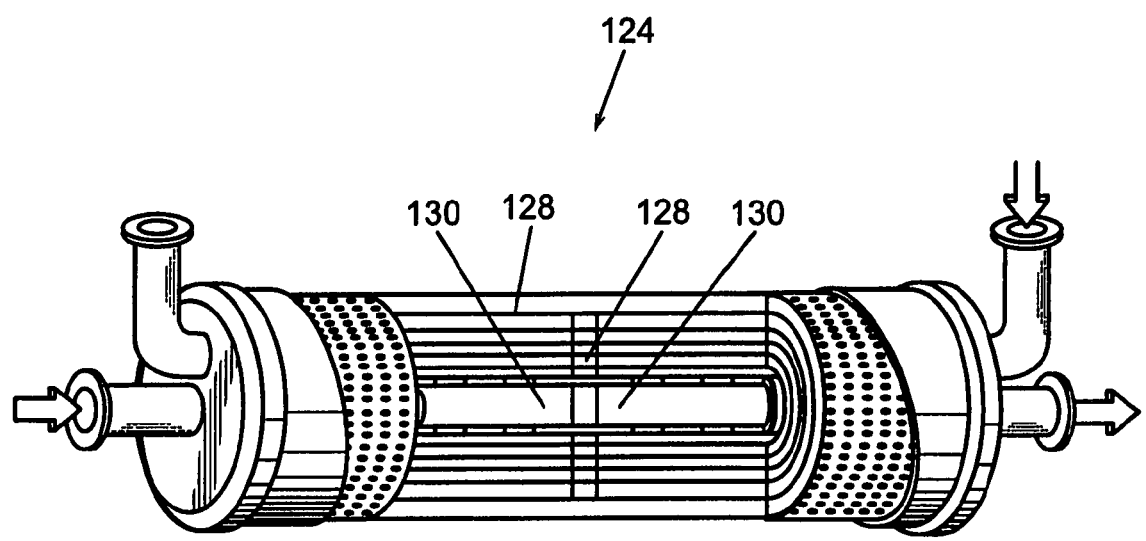
FIG. 18 is a perspective view with a partial cut away section of a HFC usable to practice the second stage of this invention.
Figure 19:
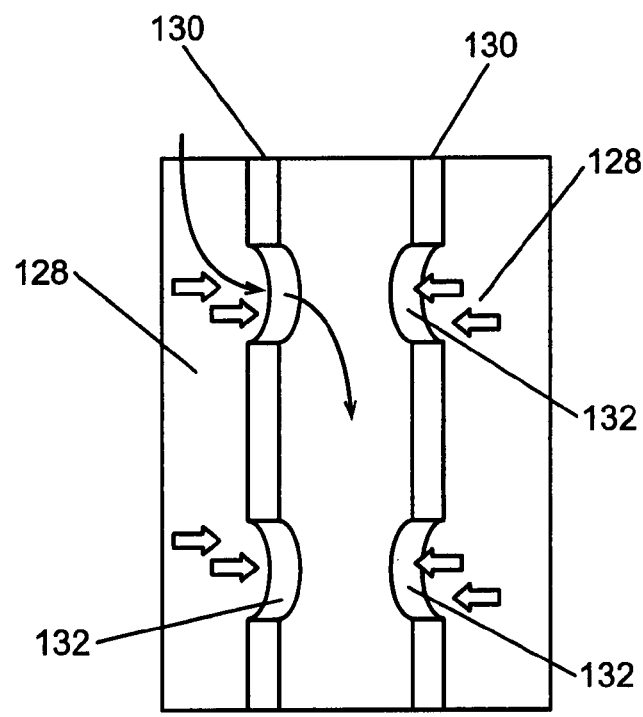
FIG. 19 is cross-sectional view of a portion of a hollow fiber membrane of the HFC shown in FIG. 18.

HFC 124 is shown in detail in FIGS. 18 and 19. HFC 126 is identical to HFC 124 and is not shown in detail for brevity. HFC 124 may be formed from a generally hollow cylindrical body having a diameter ranging between about 1½ inches to about 4 inches that forms a chamber 128 that contains a plurality, typically 3,000 to 5,000, of hollow fibers 130, which are tubes having small diameters, such as between about 0.2 mm and about 1.0 mm. However, the hollow fibers may be number one or more. Chamber 128 is the space inside the cylindrical body of HFC 124 and outside the surfaces of hollow fibers 130. Chamber 128 is commonly referred to as the shell side of the hollow fibers 130. Each hollow fiber 130, as shown in FIG. 19, is a cylindrical tube having a small diameter and is formed from a membrane having pores 132 sized to allow gases and liquids to pass through the membrane. Hollow fibers 130 are positioned in HFC 124 so that their longitudinal axes are generally parallel to the longitudinal axis of the HFC 124. Pores 132 need only be large enough to allow the extraction solvent and a gas to pass through pores 132. Pores 132 may have a diameter within the range of between about 5 kilodaltons and about 500 kilodaltons or between about 3 nanometers and about 300 nanometers. Varying the size of pores 132 can allow either more or less materials to pass through pores 132.

While not being bound by the following statements, the following discussion is a possible explanation of the operation of the system at the pores 132 of the hollow fibers. The hollow fibers 130 may be formed of either hydrophobic or hydrophilic materials. If hollow fibers 130 formed from a hydrophobic material are used, the solvent fills pores 132 and an interface forms between the solvent in pores 132 and the fluid that remains in the lumens. The solvent diffuses across the interface into the fluid, but there is minimal, if any, mixing of the fluid and the solvent. Thus, there exists very little possibility of an emulsion forming. The lipids that may have been solubilized by the action of the solvents diffuse into the solvent in the pores 130 at the interface. The lipids continue to diffuse through pores 132 until the lipids are swept away by the solvent flowing through HFCs 124 and 126 on the shell side 142 of the lumens. If a hydrophilic material is used to form hollow fibers 130, pores 132 fill with fluid, and the solvent does not fill pores 132. The lipids then diffuse through pores 132.

The preferred material is a hydrophobic material because the highest transport rate is achieved when pores 132 are filled with the material having the highest solubility for the material desired to be passed through pores 132. In this case, lipids are more soluble in the solvents described above than in the fluid. Thus, a hydrophobic material is preferred.

The flow rate of a fluid and an extraction solvent through HFC 124 dictates the required amount of permeable surface area on hollow fibers 130. For instance, the slower the flow rate, the smaller the surface area required, and, conversely, the faster the flow rate, the larger the surface area required. This is dictated by a mass transport formula. The formula below illustrates the situation for a soluble gas:

$$Q_1(C_{in} - C_{out}) = K_1 A_m \Delta C_{lm} = K_l A_m \frac{\left(C_{in} - \frac{P_{out}}{H}\right) - \left(C_{out} - \frac{P_{in}}{H}\right)}{\ln \frac{C_{in} - \frac{P_{out}}{H}}{C_{out} - \frac{P_{out}}{H}}}$$

where $C_{out}$ represents the liquid stage concentration (output), $C_{in}$ represent the liquid stage concentration (input), $K_1$ represents the overall mass transport coefficient, $A_m$ represents the total membrane contact area, $Q_1$ represents the liquid flow rate, H represents the Henry's Law coefficient and P represents the gas stage partial pressure. If $P_{in}$ and $P_{out}$ are small in magnitude and/or H is large, the terms P and H are negligible and the first equation simplifies to:

$$C_{out} = C_{in} \ln\left(-\frac{K_l A_m}{Q_1}\right).$$

Examples of commercially available HFCs are the CELGARD mini model no. G471, G476, or G478, available from CelGard, Charlotte, N.C., and the Spectrum MINI-KROS model no. M21S-600-01N, available from Spectrum Laboratories, Inc., Rancho Dominguez, Calif.

The once-through subsystem 122 includes a pervaporation buffer container 134 for receiving the fluid from first stage subsystem 12. The pervaporation buffer container 134 is coupled to a container 136, which may be, but is not limited to, an air bag for containing the air that escapes from buffer container 134. The fluid may flow into HFC 124 by gravity, pump 138, which may be a peristaltic pump or other pump not having vanes that contact the fluid being pumped, or other means.

Pervaporation buffer container 134 is coupled to the lumens of hollow fibers 130 of HFC 124 so that a fluid may flow through the lumens of hollow fibers 130 during operation. The lumens of hollow fibers 130 of HFC 124 are in fluid communication with the lumens of hollow fibers 140 of HFC 126. A chamber 142, also referred to as the shell side of hollow fibers 140 of HFC 126, is capable of receiving a gas, such as air, nitrogen, or other material, such as mineral oil or the like, for removing a solvent from the fluid. However, in another embodiment, the gas is sent through the lumens of hollow fibers 140 and the fluid is sent through HFC 126 on the shell side of hollow fibers 140. Chamber 142 of HFC 126 is coupled to a solvent removal subsystem 144 and is in. fluid communication with chamber 128 of HFC 124. Solvent removal subsystem 144 cycles a material through chambers 128 and 142 to remove the extraction solvent from the fluid contained within lumens of hollow fibers 130 and 140. In certain embodiments, the gaseous material is ambient air or nitrogen. Solvent removal subsystem 144 may also cycle a mineral oil or other material through chambers 128 and 142.

Solvent removal subsystem 144 includes a carbon bed 146, a first filter 148, a pump 150, and a second filter 152. These elements may be coupled together using a conduit, a coupling or other connection device. Carbon bed 146 is coupled to HFCs 124 and 126 for receiving materials having an extraction solvent. Carbon bed 146 removes most, and in some cases all, of the extraction solvent from the material being passed through the chambers 128 and 142 of HFCs 124 and 126. In at least one test, the concentration of solvent was reduced by at least 98 percent. First filter 148 and second filter 152 provide a sterile barrier between pump 150 and solvent removal subsystem 144, thereby allowing pump 150 to be removed. In another embodiment, the solvent removal subsystem 144 may be composed of one or more carbon beds, condensers or cold traps, or catalytic combustors to remove the solvent vapors from the gas before it is recycled through HFCs 124 and 126.

Once-through subsystem 122 also includes an output buffer container 154 for collecting the fluid after passing through the lumens of hollow fibers 130 and 140 of HFCs 124 and 126. Output buffer container 154 may be any container that is preferably sterile and capable of holding the fluid. A scale 156 may be included to determine the amount of fluid present in output buffer container 154 and for other analytical purposes.

Once-through subsystem 122 may also include at least one sensor 158 for sensing the presence of an extraction solvent in the fluid leaving once-through subsystem 122. Various types of solvent sensors may be used as sensor 158. Preferably, the sensors are capable of detecting very low levels of solvent. One such sensor is capable of measuring differences in infrared absorption spectra between solvents and plasma. Using approaches known to those skilled in the art, several light sources and detectors can be integrated into a non-contact optical sensor that can be calibrated to measure the concentrations of one or all of the solvents. Another useful sensor includes a resistive sensor that uses a resistance processor to detect the presence of very low levels of solid particles, such as model number TGS2620 or TGS822 available from Figaro USA Inc., Glenview, Ill. Yet another type of optical sensor includes one that determines or identifies molecules comprising a solvent. Optionally, indirect measurement of solvent level in the fluid could be performed by measuring the amount of solvent in solvent removal subsystem 144. However, direct measurement is more reliable, because an obstruction in filter(s) 148 or 152, or other flow impediment may falsely indicate that solvent has been extracted, when the solvent has in fact remained in the fluid.

HFCs 124 and 126 have been tested and successfully reduce total concentrations of solvents, such as di-isopropyl ether and di-ethyl ether, in water and plasmas, such as human and bovine plasma, using different HFCs, pressures, and flow rates, as shown in Table 1 below. Table 2 below shows the reduction in concentrations of DiPE in water, bovine plasma and human plasma as a function of time. HFCs 124 and 126 may have a total surface area of permeable membrane formed by the hollow fibers between about 4,200 square centimeters and about 18,000 square centimeters, depending on the type of HFC used. Further, the gas flow rate was varied between about 2 liters per minute to about 10 liters per minute, and the plasma flow rate was varied between about 10 mL per minute to about 60 mL per minute. Operating the once-through final subsystem 122 in this manner can reduce the initial concentrations of solvents from between about 28,000 parts per million (ppm) and 9,000 ppm to between about 1327 ppm and about 0.99 ppm within between about 14 minutes and 30 minutes.

TABLE 1

| Module (Quantity) | Orientation | Stage | Lumen Flow rate (cc/min) | Air Flow (L/min) | Pressure before HFC (psig) | Pressure after HFC (psig) | Carbon (g) | Volume Treated (L) | Initial DIPE conc ppm | Final DIPE conc ppm |
|---|---|---|---|---|---|---|---|---|---|---|
| *Effect of Module* | | | | | | | | | | |
| Fresenius F6 (1) & F8 (1) | Horiz | $H_2O$ | 20 | 9.3 | 0.44 | −0.74 | 100 | 0.75 | 9045 | 1327 |
| Spectrum 11200 $cm^2$ (2) | Horiz | $H_2O$ | 20 | ~9 | −0.13 | −1.01 | 100 | 0.75 | 9684 | 3 |
| Celgard (1) | Vertical | $H_2O$ | 20 | 11 | −0.2 | −1.21 | 100 | 0.5 | 10518 | 0.99 |
| Spectrum 11200 $cm^2$ (2) | Horiz | Human Plasma | 20 | 9.2 | 0.91 | −0.06 | 100 | 0.75 | 12200 | 6 |
| Celgard (2) | Vertical | Human | 20 | 10.1 | −0.16 | −1.3 | 150 | 0.25 | 27822 | 9 |
| *Effect of Flow Rate* | | | | | | | | | | |
| Spectrum 11200 $cm^2$ (2) | Horiz | $H_2O$ | 18 | | 0.71 | −0.83 | | 0.75 | 9055 | 18 |
| Spectrum 11200 $cm^2$ (2) | Horiz | $H_2O$ | 20 | | 0.65 | −0.88 | | 0.75 | 8851 | 22 |
| Spectrum 11200 $cm^2$ (2) | Horiz | $H_2O$ | 40 | | 0.7 | −0.85 | | 0.75 | 10016 | 11 |
| Spectrum 11200 $cm^2$ (2) | Horiz | $H_2O$ | 60 | | 0.65 | −0.82 | 100 | 0.75 | 10134 | 93 |
| Celgard (1) | Vertical | $H_2O$ | 20 | 9.3 | 0.44 | −0.2 | 100 | 0.75 | 7362 | 22 |
| Celgard (1) | Vertical | $H_2O$ | 40 | 9.2 | 0.44 | −0.2 | 100 | 0.75 | 9366 | 193 |
| *Effects of Pressure* | | | | | | | | | | |
| Celgard (2) | Vertical | Human | 20 | 9.7 | 0.11 | −1.33 | 100 | 0.25 | 18782 | ND |
| Celgard (2) | Vertical | Human | 20 | 9.2 | −1.39 | −2.93 | 100 | 0.25 | 15246 | ND |
| Celgard (2) | Vertical | Human | 20 | 8.1 | −2.79 | −4.12 | 100 | 0.25 | 13144 | ND |
| *Full Body Volume* | | | | | | | | | | |
| Celgard (2) | Vertical | Human | 20 | 5.3 | −1.1 | −1.8 | 300 | 3100 | 9040 | 24 |

TABLE 2

| | DIPE concentrations [ppm] | | |
|---|---|---|---|
| Time [min] | Water | Bovine | Human (Norm) |
| 0 | 6782.094027 | 9473.974574 | 11351.10738 |
| 2 | 1716.182938 | 3012.065643 | 3868.491245 |
| 4 | 118.591244 | 485.1426701 | 636.1926821 |
| 6 | 16.36572648 | 102.9572692 | 125.8618995 |
| 8 | 5.364620368 | 36.33996072 | 60.440048 |
| 10 | 4.230662874 | 16.08489373 | 34.50180421 |
| 12 | 2.019251402 | 23.54890574 | 16.71332069 |
| 14 | 1.537721419 | 9.218693213 | 17.32898791 |
| 16 | 3.169227108 | 6.549024255 | 15.26858655 |

Various control devices are included in once-through subsystem 122. For instance, once-through subsystem 122 includes fluid level sensors 160 and 162 and a temperature sensor 172 coupled to pervaporation buffer container 134, a fluid presence detector 164, an encoder 166 and a current overload detector 168 for controlling pump 138, and a pressure sensor 170. Solvent removal subsystem 144 includes a fluid presence detector 174, temperature sensors 176 and 178, a current overload detector 184 for controlling pump 150, and pressure sensors 180 and 182.

(b) Recirculating Solvent Removal Subsystem

The recirculating solvent removal subsystem 200 is configured much like the once-through subsystem 122, except for a few differences. FIG. 17 depicts the recirculating system 200 as including two HFCs 202 and 204 for removing the extraction solvent from the fluid. While the embodiment depicted in FIG. 17 includes two HFCs positioned in parallel, the subsystem may be composed of any number of HFCs positioned in parallel, series, or other configurations. In another embodiment, the subsystem may be composed of only a single HFC.

HFCs 202 and 204 are preferably sized according to the calculations and methodology set forth above. HFCs 202 and 204 contain hollow fibers 206 and 208, respectively, for receiving the fluid mixed with residual extraction solvent, from first stage subsystem 12. The fluid flows from first stage subsystem 12 to a recirculation vessel 210. Recirculation vessel 210 receives the fluid mixture from the first stage subsystem 12 and from HFCs 202 and 204. The mixture of fluid and remaining extraction solvent not removed in first stage subsystem 12 is sent to HFCs 202 and 204 using gravity flow, a pump 212, which may be a peristaltic pump or other pump not having vanes that contact the fluid being pumped, vacuum, or other means. The second mixture flows through the lumens of hollow fibers 206 and 208 of HFCs 202 and 204 while a material, such as, but not limited to, a gas, including common air, nitrogen, or other inert gas, mineral oil, or other materials, is passed through chambers 214 and 216 of HFCs 202 and 204, respectively, or vice versa. Chambers 214 and 216 are also referred to as the shell sides of HFCs 202 and 204. The mixture of the fluid and the extraction solvent is circulated between recirculation vessel 210 and HFCs 202 and 204 until a sensor 218 detects that the concentration of extraction solvents in the fluid is less than a selected acceptable level. The fluid is then sent to output buffer container 220 by closing valve 222 and opening valve 224. The amount of fluid present in output buffer container 220 may be determined using scale 226.

The recirculating solvent removal subsystem 200 also includes a number of control devices. For instance, the recirculating solvent removal subsystem 200 includes fluid level sensors 228 and 230, fluid presence detectors 232 and 233, a current overload detector 234 and an encoder 236 for controlling pump 212, a pressure sensor 238, and a temperature sensor 240. These sensing devices are used for controlling the subsystem 200.

A solvent removal system 242 is included within the recirculating subsystem 200 for removing the extraction solvent from a material, such as air, nitrogen or other inert gas, mineral oil, or other materials. Solvent removal system 242 sends the material containing the solvent through recirculation vessel 210 to allow more solvent from the fluid contained in vessel 210 to be removed, if desired. Solvent removal system 242 includes a carbon bed 244 for removing the solvents from the material, and a first filter 246 and a second filter 248 for creating a sterile barrier around pump 250 so that pump 250 may be removed without contaminating solvent removal system 242. In an alternative embodiment, solvent removal system 242 may be composed of one or more carbon beds, condensers or cold traps, or catalytic combustors to remove the solvent vapors from the gas before it is recycled through HFCs 202 and 204. A pump 250 may be provided for circulating the gas through the subsystem. Solvent removal system 242 may also include pressure sensors 252 and 254, and a current overload sensor 256 for controlling pump 250.

HFCs 202 and 204 have been tested and successfully reduce total concentrations of solvents, such as di-isopropyl ether and di-ethyl ether, in water and plasmas, such as human and bovine plasma, as shown in Table 3 below. HFCs 202 and 204 may have a total surface area of permeable membrane formed by the hollow fibers between about 4,200 square centimeters and about 18,000 square centimeters, depending on the type of HFC used. Further, the gas flow rate was varied between about 2 liters per minute to about 14 liters per minute, and the plasma flow rate was varied between about 9 mL per minute to about 900 mL per minute. Operating the recirculating subsystem 200 in this manner can reduce the initial concentrations of solvents, such as DiPE and DEE, from between about 31,000 ppm and 9,400 ppm to between about 312 ppm and about 2 ppm within between about 14 minutes and 80 minutes.

TABLE 3

| Lumen Material | Solvent to be Removed | Shell Material | Shell Flow | Lumen Flow | Module (Surface Area) | Initial Solvent Conc (ppm) | Final Solvent Conc (ppm) | Time recirculating |
|---|---|---|---|---|---|---|---|---|
| Water | Diethyl Ether | Air | 7 L/min | 220 | Fresenius F80A (18000 cm2) | 31000 | 265 | 30 min |
| Water | Diisopropyl Ether | Air | 12.3 L/min | 750 | Celgard (8400 cm2) | 6782 | 2 | 14 min |

TABLE 3-continued

| Lumen Material | Solvent to be Removed | Shell Material | Shell Flow | Lumen Flow | Module (Surface Area) | Initial Solvent Conc (ppm) | Final Solvent Conc (ppm) | Time recirculating |
|---|---|---|---|---|---|---|---|---|
| Bovine Plasma | Diisopropyl Ether | Air | 12.3 L/min | 750 | Celgard (8400 cm2) | 9473 | 7 | 16 min |
| Human Plasma | Diisopropyl Ether | Air | 12.3 L/min | 750 | Celgard (8400 cm2) | 11351 | 15 | 16 min |
| Water | Diisopropyl Ether | Heavy Mineral Oil | 10 cc/min | 4 cc/min | Spectrum (8000 cm2) | 4635 | 312 | 80 min |

(c) Operation of the Second Stage Subsystem

Second stage subsystem 120 receives a mixture of a fluid and an extraction solvent from first stage subsystem 12. Second stage subsystem 120 removes a portion of the extraction solvent so that the fluid may be administered to a patient without the patient experiencing undesirable consequences. The solvent may be recovered, recirculated, collected for future use, or discarded.

In second stage subsystem 120, the mixture of fluid and extraction solvent is sent through at least one HFC where the mixture contacts a material for removing the solvent. This material may be a gas, such as air or nitrogen, mineral oil, or other material. When a gas is used, the gas fills the pores of the membranes forming the hollow fibers of the HFCs. The solvent diffuses through the pores of the hollow fibers and dissolves into the gas flowing around the hollow fibers on the shell side of the hollow fibers. In other words, the gas volatilizes at the wall of the fiber, the solvent diffuses into the gas, and the gas containing solvent is carried away with the flow of the gas.

Typically, the hollow fibers of the HFCs may be adjusted to prevent the fluid from passing through the pores and the gas from passing through the pores and forming a droplet in the fluid. Factors capable of being adjusted include surface chemistry, surface tension, trans-membrane pressure, temperature, fluid flow rate, choice of material, and the like. Alternatively, these factors can be adjusted to allow the fluid to enter the pores of the HFC rather than the gas. In one embodiment, the hollow fibers of the HFCs are hydrophobic and prevent the fluid from diffusing through the pores; however, the hollow fibers may be hydrophilic, as described above. Advantageously, hydrophobic fibers provide a more robust membrane, and the trans-membrane pressure is not as critical.

Further, the pores of the HFCs need only be large enough to allow for the solvent diffusion through the pores. The solvent is typically volatile in the gas, which means that resistance to solvent transfer is most significant at the inside wall of the fibers. Typically, resistance to solvent transfer is a mathematical function of fluid velocity in the lumens of the hollow fibers raised to the one third power.

Solvent removal subsystems 144 and 242 may be utilized to remove an extraction solvent from the material carrying the solvent. Solvent removal subsystems 144 and 242 circulate the material through the shell side of the hollow membranes of the HFCs to remove the solvent from the fluid in the lumens of the HFCs and through the carbon beds, filters and other devices to remove the solvent from the gas. The gas containing solvents may be passed across a cold surface to condense water. The cold surface may be formed from a metal plate, such as, but not limited to, a solid-state Peltier condenser, which typically has an operating temperature ranging between about 0° C. to about 5° C. The de-watered gas is then sent to a device, such as a carbon bed, for removing the solvent from the gas. Alternatively, the gas containing solvents may be sent directly to a carbon bed without first passing through a condenser. A sensor may be positioned within solvent removal subsystem to detect the presence of solvent in the gas. The plasma is circulated through at least one HFC until the solvent sensor indicates that the concentration of solvent in the fluid has been reduced below a particular threshold enabling the fluid to be administered to a patient without undesirable consequences.

3. Exemplary Embodiment

Figure 21:
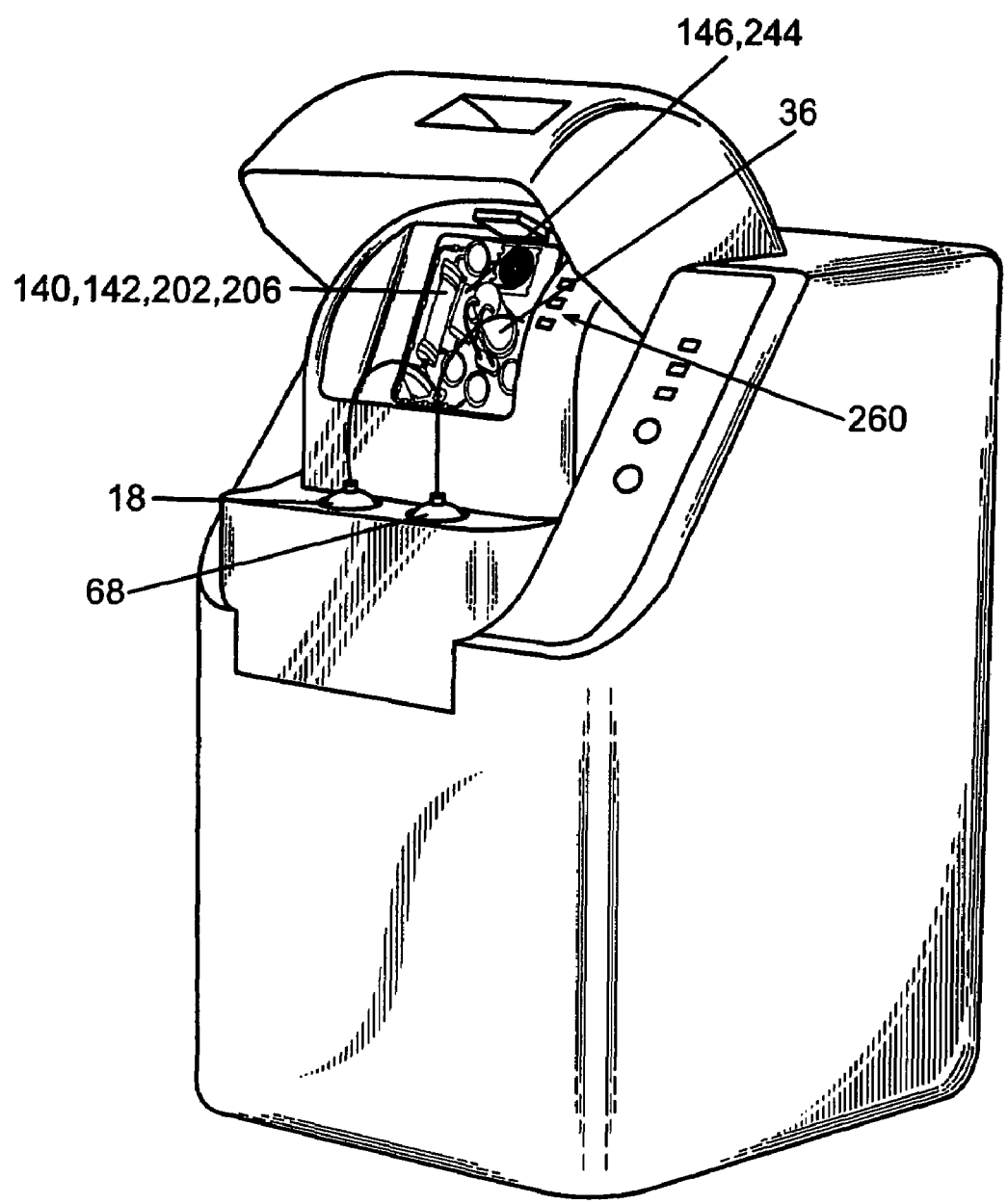
FIG. 21 is a perspective view of the module of FIG. 20 coupled to a delipidation system.

The embodiments described above may be manufactured so that all components that come in contact with a fluid during operation are contained within a single module that may be disposable. The embodiment shown in FIGS. 2 and 16 or 17 may be assembled in a module 260, as depicted in FIGS. 20 and 21. Modules 260 contain components of delipidation system 10 through which the fluid flows. To prevent the spread of diseases and for other health reasons, delipidation system 10 should be cleaned after each use before being used with a fluid from a different source. In one embodiment, modules 260 are disposable, which enables the system to be set up quickly after having been used. Delipidation device 10 may be prepared for use with another patient's fluid by simply removing and disposing a used module 260 in a trash receptacle and replacing it with a sterile module that may have never been used or may have been sterilized since a prior use.

4. EXAMPLES AND RESULTS OF USE (a) First Example

In accordance with the process described above and the embodiments, shown in FIGS. 2 and 3, human plasma was delipidated in an apparatus according to this invention by first introducing the plasma into a homogenizer with an equal volume of di-isopropyl ether (DIPE). The homogenizer used was a T25 UltraTurrax with a 25 mm diameter rotor head available from IKA Works of Germany. The homogenizer generated droplets having a diameter of about 5 um. The fluids were homogenized for about 6 minutes while the dispersion head rotated at about 24,000 rpm. The delipidated plasma containing residual delipidating solvent was then introduced into a solvent extraction device that resembled the subsystem shown in FIG. 17. The fluid was circulated through the hollow fibers of the HFCs at a flow rate of about 750 ml/min. Each HFC had a hold-up volume of about 50 ml and an area of about 4,800 $cm^2$. Air was circulated through the shell of the HFC to extract the residual delipidating solvent from the fluid. A solvent removal subsystem was utilized to remove the solvent from the gas. The gas was sent through a carbon bed to remove the remaining solvent from the gas. Upon indication that sufficient levels of solvent were removed, as measured by gas chromatography, the fluid was then tested to determine the effectiveness of the apparatus.

Delipidation of total cholesterol was greater than 90%, as measured by standard lipid profile enzymatic assays. Further, the process removed more than 60% of triglycerides and over 90% of high density lipoproteins while minimizing the reduction of apolipoproteins. For a volume of approximately 250 ml of plasma, the delipidation process as described above took approximately 20 minutes. Thus, the process produced a delipidated fluid at a rate of about 12.5 ml/min.

(b) Second Example

This same apparatus was used to delipidate human plasma through numerous experiments. The speed of the homogenizer was varied between about 13,050 rpm and about 27,050 rpm and ran for between about one minute and about four minutes. This equated to an addition of 0.05 watts of energy per ml of solvent and fluid while running the homogenizer at about 13,050 rpm, and an addition of about 0.91 watts of energy per ml of solvent and fluid while running the homogenizer at about 27,050 rpm. The amounts of materials removed are the percentages of total concentrations of materials removed from initial concentrations of the materials in the fluid after running the homogenizer for about four minutes. The amount of cholesterol removed from the human plasma ranged between about 62.2% to about 91.5% for homogenizer speeds varied between about 13,050 rpm and about 27.050 rpm, respectively. The amount of triglycerides removed from the human plasma ranged between about 35.6% and about 83.8% for homogenizer speeds varied between about 13,050 rpm and about 27,050 rpm, respectively. The amount of lipoproteins removed from the human plasma ranged between about 85.8% and about 93.1% for homogenizer speeds varied between about 13,050 rpm and about 27,050 rpm, respectively. The amount of phospholipids removed from the human plasma ranged between about 15.4% and about 23.7% for homogenizer speeds varied between about 13,050 rpm and about 27,050 rpm, respectively. The amount of apolipoprotein A1 removed from the human plasma ranged between about 4.7% at about 22,050 rpm and about 5.9% at about 18,000 rpm. The amount of apolipoprotein B removed from the human plasma ranged between about 27.6% and about 81.7% for homogenizer speeds varied between about 13,050 rpm and about 27,050 rpm, respectively.

The same apparatus was used to delipidate human plasma while running the homogenizer between speeds of about 13,050 rpm and about 27,050 rpm and for about 1 minute. The amount of cholesterol removed from the human plasma ranged between about 39.9% to about 67.3% for homogenizer speeds varied between about 13,050 rpm and about 27,050 rpm, respectively. The amount of triglycerides removed from the human plasma ranged between about 24.5% and about 53.1% for homogenizer speeds varied between about 13,050 rpm and about 27,050 rpm, respectively. The amount of lipoproteins removed from the human plasma ranged between about 70.5% and about 82.9% for homogenizer speeds varied between about 13,050 rpm and about 27,050 rpm, respectively. The amount of phospholipids removed from the human plasma ranged between about 6.3% and about 26.5% for homogenizer speeds varied between about 13,050 rpm and about 27,050 rpm, respectively. The amount of apolipoprotein A1 removed from the human plasma ranged between about 3.7% at about 27,050 rpm and about 6.7% at about 18,000 rpm. The amount of apolipoprotein B removed from the human plasma ranged between about 8.5% and about 46.7% for homogenizer speeds varied between about 13,050 rpm and about 27,050 rpm, respectively.

(c) Third Example

Using a vortexer, as shown in FIGS. 7-9, human plasma was delipidated numerous times under various conditions. The amount of cholesterol, triglycerides, lipoprotein, phospholipids, apolipoprotein A1 and apolipoprotein B removed after adding 0.1 watts of energy per ml of fluid and solvent was about 30% after 10 minutes of running the vortexer, about 60% after 20 minutes, and about 90% after 30 minutes.

The percentages of constituents removed from the fluid differ when 1.0 watt of energy per milliliter of fluid and solvent was added using the vortexer. Specifically, the percentage of cholesterol removed from the fluid after one minute was about 67.3%, after two minutes was about 80.8%, after about 3 minutes was about 88.7%, after about 4 minutes was about 91.5%, and after about 8 minutes was about 95%. The percentage of triglycerides removed from the fluid after about one minute was about 53.1%, after about two minutes was about 64.6%, after about three minutes was about 76.6%, after about four minutes was about 83.8%, and after about 8 minutes was about 88%. The percentage of lipoproteins removed after about 1 minute was about 82%, after about two minutes was about 92.9%, after about three minutes was about 92.8%, after about four minutes was about 92.6%, and after about eight minutes was about 95%. The percentage of phospholipids removed after about one minute was about 24.2%, after about two minutes was about 23.3%, after about three minutes was about 23.9%, after about four minutes was about 23.7%, and after eight minutes was about 24%.

The terms and expressions which have been employed herein are used as terms of description and not of limitation, and there is no intention, in the use of such terms and expressions, of excluding any equivalents of the features shown and described or portions thereof Having thus described the invention in detail, it should be apparent that various modifications can be made in the present invention without departing from the spirit and scope of the following claims.

We claim:

1. A system for removing at least one lipid from a fluid containing lipids or lipid-containing organisms, comprising:
   an extraction solvent source containing an extraction solvent;
   a delipidation device that receives a mixture of the fluid and the extraction solvent and dissolves at least a portion of the lipids;
   a solvent removal subsystem coupled to the delipidation device such that the solvent removal subsystem receives at least a portion of the mixture from the delipidation device, the solvent removal subsystem comprising:
      a recirculating vessel with at least two inlet ports and an outlet port;
      an output buffer container;
      at least one hollow fiber contactor;
      a sensor coupled to a conduit disposed adjacent the outlet port of the recirculating vessel and configured to detect a level of the extraction solvent within the portion of the mixture; and at least one valve positioned adjacent the sensor that directs the portion of the mixture exiting the outlet port of the recirculating vessel (i) to the output buffer container when the extraction solvent level detected by the sensor is below the predetermined threshold and (ii) to the at least one hollow fiber contactor when the extraction solvent level detected by the sensor is above the predetermined threshold.

2. The system of claim 1, wherein the delipidation device comprises at least one homogenizer.

3. The system of claim 2, wherein the delipidation device further comprises a centrifuge coupled to the at least one homogenizer.

4. The system of claim 1, wherein the at least one hollow fiber contactor comprises at least two hollow fiber contactors coupled together in parallel.

5. The system of claim 1, wherein the at least one hollow fiber contactor comprises at least two hollow fiber contactors coupled together in series.

6. The system of claim 1, wherein the sensor is a solvent vapor detector.

7. The system of claim 1, wherein the at least one valve comprises two two-way valves.

8. The system of claim 1, further comprising a fluid source containing the fluid.

9. The system of claim 8, wherein the fluid source comprises a device for removing plasma from blood.

10. The system of claim 8, further comprising:
a first pump disposed between the fluid source and the delipidation device that transfers the fluid to a location to mix with the extraction solvent; and
a second pump disposed between the extraction solvent source and the delipidation device that transfers the extraction solvent to the location.

11. The system of claim 10, wherein the location is upstream from an input of the delipidation device.

12. The system of claim 10, wherein the location is the delipidation device.

13. A method for removing at least one lipid from a fluid containing lipids or from lipid-containing organisms, comprising:

supplying the fluid from a fluid source;

supplying an extraction solvent from an extraction solvent source;

mixing the fluid and the extraction solvent to form a mixture;

separating the mixture into three layers comprising a first layer of the fluid with a first portion of the extraction solvent and at least some lipids therein, a second layer of free lipids, and a third layer of a second portion of the extraction solvent with dissolved lipids; and passing the first layer to a solvent removal subsystem, the solvent removal subsystem comprising a sensor, at least one valve, an output buffer container, and at least one hollow fiber contactor;

the sensor determining a level of the extraction solvent in the first layer;

the at least one valve directing the first layer to the at least one hollow fiber contactor when a level of the extraction solvent detected by the sensor is above a predetermined threshold; and the at least one valve directing the first layer to the output buffer container when a level of extraction solvent detected by the sensor is below a predetermined threshold.

14. The method of claim 13, wherein mixing the fluid and the extraction solvent to form a mixture comprises mixing the fluid and the extraction solvent at a location upstream an input of a delipidation device.

15. The method of claim 13, wherein mixing the fluid and the extraction solvent to form a mixture comprises mixing the fluid and the extraction solvent within the delipidation device.

* * * * *